United States Patent [19]

Sharpless et al.

[11] Patent Number: 5,767,304
[45] Date of Patent: Jun. 16, 1998

[54] CATALYTIC ASYMMETRIC AMINOHYDROXYLATION OF OLEFINS WITH CARBAMATES

[75] Inventors: K. Barry Sharpless; Guigen Li, both of La Jolla, Calif.

[73] Assignee: The Scripps Research Institute, La Jolla, Calif.

[21] Appl. No.: 651,104

[22] Filed: May 21, 1996

[51] Int. Cl.[6] .................................................. C07C 271/16
[52] U.S. Cl. ........................... 560/27; 560/29; 560/115; 560/160
[58] Field of Search .......................... 560/29, 160, 115, 560/27

[56] References Cited

PUBLICATIONS

Berrisford, et al., "Ligand–Accelerated Catalysis", *Angew. Chem. Int. Ed. Engl.*, 34:1059–1070 (1995).

Fukuyama, et al., "2"–and 4–Nitrobenzenesulfonamides: Exceptionally Versatile Means for Preparation of Secondary Amines and Protection of Amines", *Tetrahedron Letters*, 36:6373–6374 (1995).

Hentges, et al., "Improved Procedure for the Oxyamination of Olefins with Trioxo–(tert–butylimido)osmium(VIII)", *J. Org. Chem.*, 45:2257–2259 (1980).

Herranz, et al., "Osmium–Catalyzed Vicinal Oxyamination of Olefins by N–Chloro–N–Argentocarbamates: Ethyl . . ." *Org. Syntheses*, 61: 223–226 (1981).

Herranz, et al., "Osmium–Catalyzed Vicinal Oxyamination of Olefins by N–Chloro–N–argentocarbamates", *J. Am. Chem. Soc.*, 100: 3596–3598 (1978).

Herranz, et al. "Osmium–Catalyzed Vicinal Oxyamination of Olefins by N–Chloro–N–metallocarbamates", *J. Org. Chem.*, 45:2710–2713 (1980).

Li, et al., "Catalytic Asymmetric Aminohydroxylation (AA) of Olefins", *Angew. Chem. Int. Ed. Engl.*, 35:451–4453 (1996).

Li, et al., "Catalytic Asymmetric Aminohydroxylation Provides a Short Taxol Side–chain Synthesis", *Acta Chemica Scandinavica*, 50:649–651 (1996).

Mangatal, et al., "Application of the Vicinal Oxyamination Reaction with Asymmetric Induction . . . " *Tetrahedron*, 45:4177–4190 (1989).

Patrick, et al., "Stereospecific Vicinal Oxyamination of Olefins by Alkylimidoosmium Compounds", *J. Org. Chem.*, 43:2628–2638 (1978).

Sharpless, et al., "A New Reaction. Stereospecific Vicinal Oxyamination of Olefins by Alkyl Imido Osmium Compounds", *J. Am. Chem. Soc.*, 97:2305–2307 (1975).

Sharpless, et al., "Osmium–Catalyzed Vicinal Oxyamination of Olefins by Chloramine–T", *J. Org. Chem.*, 41:177–179 (1976).

*Primary Examiner*—Joseph Conrad
*Attorney, Agent, or Firm*—Donald G. Lewis

[57] ABSTRACT

β-Hydroxyamines and β-hydroxycarbamates are synthesized from olefin substrates by means on a catalyzed asymmetric addition reaction. The addition reaction is catalyzed by osmium and is co-catalyzed by chiral ligands. The chiral ligands, in addition to being co-catalysts with the osmium, also serve to direct the addition reaction regioselectively and enantioselectively. Divalent ligands are preferred over monovalent ligands because of their enhance regio- and enantio-selectivity. Carbamates are employed as an oxidant nitrogen source for the production of β-hydroxysulfonamides. Excellent yields and enantiomeric efficiencies are achieved with co-solvents containing a 50/50 (v/v) mixtures of water and organic solvent. The performance of the reaction is further enhanced by omitting the addition silver or mercurial salts conventionally employed in asymmetric aminohydroxylation additions to olefins performed in neat or substantially neat solvents. β-Hydroxyamines are then obtained by deprotecting the corresponding β-hydroxycarbamate.

4 Claims, 29 Drawing Sheets

| Entry | Substrate | Product | %ee (DHQ)₂PHAL | %ee (DHQD)₂PHAL | Yield (%) | Time (h) |
|---|---|---|---|---|---|---|
| 1 | Ph⁀CO₂CH₃ | ZNH, Ph, CO₂CH₃, OH  1 | 94 | 97 | 55 | 1.5 |
| 2 | Me-Ar-CO₂CH₃ | Me, ZNH, CO₂CH₃, MeOH  2 | 94 | 82 | 61 | 2 |
| 3[a] | H₃CO₂C⁀CO₂CH₃ | ZNH, H₃CO₂C, CO₂CH₃, OH  3 | 84 | 87 | 55 | 24 |
| 4 | cyclohexene | ZNH, OH  4 | 63 | 56 | 51 | 2 |
| 5[b] | Ph⁀Ph | ZNH, Ph, Ph, OH  5 | 91 | 88 | 92 | 3 |
| 6[b] | naphthyl-CH=CH₂ | ZNH, OH, naphthyl  6 | 99 | 99 | 70 | 3 |

FIG. 2 a. CH₃CN/H₂O was used as the solvent; b. the reaction was run at 0 °C.
c. Z = (EtO₂C)

PHAL

DP-PHAL

DPP

PYR

IND

AQN (3a, 3b)

Alk* =

Dihydroquinidyl (DHQD)

or

Dihydroquinyl (DHQ)

Dihedral angles:

C1-Os-N-C2 = -0.7°
Os-N-C2-C1 = 0.9°
N-C2-C1-Os = -0.8°
C2-C1-Os-N = 0.7°

C1-Os-N-C2 = -2.1°
Os-N-C2-C1 = 2.7°
N-C2-C1-Os = -2.5°
C2-C1-Os-N = 2.0°

Bond angles:

C1-Os-N = 63.6°
Os-N-C2 = 104.4°
N-C2-C1 = 96.5°
C2-C1-Os = 95.4°
Os-N-S = 130.5°
S-N-C2 = 116.5°

C1-Os-N = 64.1°
Os-N-C2 = 103.5°
N-C2-C1 = 97.8°
C2-C1-Os = 94.5°
Os-N-S = 136.4°
S-N-C2 = 120.0°

N-Methylsulfonyl-
osmaazetidine

N-Methoxycarbonyl-
osmaazetidine (Becke3LYP, LanL2DZ basis set)

| Substrate | Product | (DHQ)₂-PHAL | | (DHQD)₂-PHAL | | Time (hr) |
|---|---|---|---|---|---|---|
| | | %ee | % yield | %ee | % yield | |
| (alkene) | HNCOOEt / OH structure 15 | 57 | 63 | 64 | 60 | 1.5 |
| Ph-(alkene) | HNCOOEt / Ph / OH structure 16 | 73 | 46 | 82 | 49 | 1 |

FIG. 16

| Substrate | Product | %ee (DHQ)$_2$-PHAL | %ee (DHQD)$_2$-PHAL | Yield (%) | Time (h) |
|---|---|---|---|---|---|
| | ab | 94 | 97 | 55 | 1.5 |
| | 2b | 94 | 82 | 61 | 2 |

FIG. 23

| Substrate | Product | %ee (DHQ)$_2$-PHAL | %ee (DHQD)$_2$-PHAL | Yield (%) | Time (h) |
|---|---|---|---|---|---|
| H$_3$CO$_2$C–CH=CH–CO$_2$CH$_3$ | 3b (H$_3$CO$_2$C–CH(NHCO$_2$Bn)–CH(OH)–CO$_2$CH$_3$) | 84 | 87 | 55 | 24 |
| cyclohexene | 4b (2-(BnO$_2$C-NH)-cyclohexan-1-ol) | 63 | 56 | 51 | 2 |

FIG. 24

| Substrate | Product | %ee (DHQ)₂-PHAL | %ee (DHQD)₂-PHAL | Yield (%) | Time |
|---|---|---|---|---|---|
| 2-vinylnaphthalene | compound 6 (HN-CO₂Bn, OH) | 99 | 99 | 70 | 3 h |
| styrene | compound 20, >5:1 regioselectivity | 89 | 82 | >50 | 5–10 min |
| 4-methoxystyrene | compound 21, 10:1 regioselectivity | 96 | 89 | >60 | 10 min |

Vinylnaphthalene at 0 °C; all other at room temperature

FIG. 26

CATALYTIC ASYMMETRIC AMINOHYDROXYLATION OF OLEFINS WITH CARBAMATES

FIELD OF INVENTION

The invention relates to the regio-selective and enantio-selective conversion of olefins to β-hydroxyamines and β-hydroxycarbamates. More particularly, the invention relates to catalytic asymmetric additions or aminohydroxylations of olefins and other unsaturated substrates using carbamate as an oxidizing agent in the presence of an osmium catalyst and a chiral ligand.

BACKGROUND

Over the past 20 years, separate and distinct synthetic methodologies have been developed by Sharpless et al. for the vicinal hydroxyamination of olefins. There are three major groups of oxyamination procedures which produce aminoalcohols (Sharpless et al. J. Am. Chem. Soc. 1975, 97, 2305; Sharpless et al. J. Org. Chem. 1978, 43, 2628; Sharpless et al. J. Org. Chem. 1980, 45, 2257), hydroxysulfonamides (Sharpless et al. J. Org. Chem. 1976, 41, 177; Sharpless et al. J. Org. Chem. 1978, 43, 2544; Sharpless et al. J. Org. Chem. 1979, 44, 1953; Sharpless et al. Org. Syn. 1980, 61, 85) or hydroxycarbamates (Sharpless et al. J. Am. Chem. Soc. 1978, 100, 3596; Sharpless et al. J. Org. Chem. 1980, 45, 2710; Sharpless et al. U.S. Pat. Nos. 4,871,855; 4,965,364; 5,126,494; EP 0 395 729). Each oxyamination procedure has unique reaction conditions and includes variations in solvents, auxiliary salts, nucleophiles, temperature, stoichiometric v. catalytic amounts of osmium species and stoichiometric v. catalytic amounts of ligand. Each procedure is highly dependant on the nature of the substrate and possesses unique properties which afford different yields, chemoselectivities, stereoselectivities, regioselectivities and enantioselectivitive outcomes.

1. Aminoalcohols

The first reported oxyamination procedure (Sharpless et al. J. Am. Chem. Soc. 1975, 97, 2305) generated aminoalcohols from mono and di substituted olefins, using stoichiometric quantities of a tri-oxo(tert-butylimido)osmium species. The procedure required reductive cleavage of the osmate ester which was performed with lithium aluminum hydride and afforded tertiary vicinal aminoalcohols. Yields were good to excellent, but in some cases, the side product vicinal diol was formed as an undesired by-product. The stereochemistry of addition, in methylene chloride or pyridine, was exclusively cis (Sharpless et al. J. Org. Chem. 1978, 43, 2628). In addition, the carbon-nitrogen bond formed was, in every case, at the least substituted olefinic carbon atom. Di and tri-substituted olefins reacted much slower with the generated imido reagent than with monosubstituted alkenes; tetrasubstituted alkenes yielded only the corresponding diol. However, by using a coordinating solvent such as pyridine, higher yields and higher ratios of aminoalcohol to diol were reported. Sharpless et al. J. Org. Chem. 1980, 45, 2257; Sharpless et al. J. Org. Chem. 1976, 41, 177; Sharpless et al. J. Org. Chem. 1978, 43, 2544.

2. Hydroxysulfonamides

Sharpless et al. first demonstrated that hydroxysulfonamides could be obtained using either stoichiometric or catalytic amounts of 1% osmium tetraoxide in the presence of 1.5–5 equivalents of Chloramine-T trihydrate ($TsSO_2NClNa.3H_2O$, Ts=tosylate; commercially obtained) to effect cis addition of a hydroxyl (OH) and an arylsulfonamide moiety (Ar—$SO_2NH$) across a mono or disubstituted olefinic linkages (Sharpless et. al. J. Org. Chemistry 1976, 41, 177).

Two procedures were developed to effect hydroxyamination of olefins using sulfonamides. (Sharpless et al. Org. Syn. 1980, 61, 85). The first procedure used phase transfer catalysis conditions at 55–60 EC with 1% $OsO_4$, 1:1 v/v, 0.20 Molar $CHCl_3/H_2O$, and benzyltriethylammonium chloride as the phase transfer catalyst. The chloramine T-trihydrate ($TsSO_2NClNa.3H_2O$) was either added directly or formed in situ in water; this solution was then directly used in the phase transfer mixture. The in situ procedure, for generating the chloramine salts, involved stirring a suspension of the arylsulfonamide with an equivalent of sodium hypochlorite (Clorox) until a homogenous solution was obtained. The yields were comparable with those obtained with isolated chloramine salts and the procedure was found most effective for monosubstituted and 1,2 disubstituted olefins. The phase transfer method, however, gave poor results with trisubstituted and 1,1-disubstituted olefins and the procedure did not succeed with diethyl fumarate and 2-cyclohexen-1-one. Sharpless et al. J. Org. Chem. 1978, 43, 2544.

A second procedure was carried out in tert-butyl alcohol at 55–60 EC with 1% $OsO_4$, silver nitrate (with or without) and commercially obtained chloramine T-trihydrate ($TsSO_2NClNa.3H_2O$) which provided the only source of water. The procedure did not succeed with tetramethylethylene and cholesterol, and negative results were found with most hindered tri- and tetrasubstituted olefins. Sharpless et. al. J. Org. Chemistry 1976, 41, 177; Sharpless et al. Org. Syn. 1980, 61, 85. The addition of divalent metal salts such as $AgNO_3$ and $Hg(NO_3)_2$ improved some reactions, however, other reactions suffered deleterious effects from the addition of the metal salts. Sharpless et al. J. Org Chem. 1978, 43, 2544; Sharpless et. al. J. Org. Chemistry 1976, 41, 177.

Further elaboration on either procedure showed that other sulfonamide derivatives ($ArSO_2NClNa$) could be successfully employed in addition to chloramine T, where Ar=phenyl, o-tolyl, p-chlorophenyl, p-nitrophenyl, and o-carboalkoxyphenyl. Sharpless et al. J. Org. Chem. 1978, 43, 2546.

Neither the phase transfer catalyst or tert-butyl alcohol procedures succeeded with tetramethyl ethylene, 2,3-dimethyl-2-octene, diethyl fumarate, or 2-cyclohexen-1-one. Negative results were also obtained with most hindered tri- and tetrasubstituted olefins. Herranz E., MIT Ph.D. Thesis, 1979, 33.

Solvent conditions for the synthesis of the hydroxysulfonamides included organic solvents such as acetonitrile, tert-butyl alcohol, isopropyl alcohol and chloroform which was in contact with the aqueous phase in the phase transfer catalyst procedure.

The tert-butyl alcohol procedure (including other solvents used) was not run with added water; the phase transfer catalyst (PTC) procedure required a biphasic mixture of 1:1 v/v chloroform/water. Recently, however, an improvement was reported which used a 1:1 ratio of organic solvent to water in a homogeneous, rather than a biphasic solution or organic solvent with small amounts of water. These conditions were found to provide optimum enantioselectivity, regioselectivity and improved yields from either the previously described t-butyl alcohol or PTC conditions. Sharpless et al. Angew. Chemie Intl Ed. 1996, 35, 451.

The use of chiral ligands with sulfonamides provides enantioselectivity and has been observed to both accelerate and decelerate the rate of catalysis. The hydroxysulfonamide process is a stereoselective cis process. The presence of ligands also has a dramatic effect on the regioselectivity. In a study with no ligand present with methyl cinnamate, the two regioisomers were present in a 2:1 ratio. With the addition of ligand, the ratio was improved to 5:1 or greater. Another positive effect of the ligand was its ability to suppress formation of diol by-product. Angew. Chemie Intl Ed. 1996, 35, 451.

Preferred ligands for use with sulfonamides have included the use of monovalent cinchona alkaloids or the bivalent phthalazine based, commercially available $(DHQ)_2PHAL$ and $(DHQD)_2PHAL$ alkaloids. Sharpless et al. Angew. Chemie Intl Ed. 1996, 35, 451.

Temperature conditions for the hydroxysulfonamide asymmetric aminohydroxylations have varied from 60 EC to 25 EC for reactions including sulfonamides, auxiliary salts, ligands, phase transfer catalysts and stoichiometric or catalytic osmium species, primarily in organic solvents with small amounts of water. Recently, it has been shown that temperature can been lowered to 0 EC while running the reaction, to obtain product by filtration; many hydroxysulfonamides tend to be highly crystalline Sharpless et al. Acta Chemica Scandinavica 1996 in press.

Cleavage of the sulfonamides, to free aminoalcohols, have been accomplished via standard deprotection conditions including dissolving metals (Na, $NH_3$; Sharpless et al J. Org. Chem 1976, 41, 177) and HBr, acetic acid and phenol (Fukuyama et al. Tetrahedron Lett. in press).

3. Hydroxycarbamates

A drawback with the hydroxysulfonamide procedure was that cleavage conditions were too strong for some substrates. The use of carbamates to protect the nitrogen, however, provided a methodology which avoided the use of harsh acids or reducing deprotection problems found with hydroxysulfonamides (Sharpless et al. J. Am. Chem. Soc. 1978, 100, 3596; Sharpless et al. J. Org. Chem. 1980, 45, 2710; Sharpless et al. Org. Syn. 1981, 61, 93; Sharpless et al. U.S. Pat. Nos. 4,871,855; 4,965,364; 5,126,494; EP 0 395 729).

Sharpless first demonstrated the synthesis of hydroxycarbamates with the use of N-chloro-N-argentocarbamates (Sharpless et al J. Am. Chem. Soc. 1978 100, 3596). The N-chloro-N-argentocarbamates were generated in situ via the addition of N-chlorosodiocarbamates and silver nitrate to a solution of the olefin in acetonitrile or tert-butanol with trace amounts of water (4.5 molar equivalents based on olefin) and 1% of osmium tetroxide catalyst to generate vicinal hydroxycarbamates in generally good yields. The methodology was reported to be more effective with electron deficient olefins such as dimethyl fumarate and trisubstituted olefins were reported to be less readily oxyaminated with N-chloro-N-argentocarbamates than with the chloramine-T procedures (Sharpless et. al. J. Org. Chem. 1976, 41, 177).

Sodio-N-chlorocarbamates were always first converted to either argento or mercurio salt analogs. The addition of the $AgNO_3$ or $Hg(NO_3)_2$ salts, to make N-chloro-N-argentocarbamates or mercurio salt analogs, was crucial for the reaction to retain its desired properties. (Sharpless et al J. Org. Chem., 1980, 45, 2711). This was in contrast to the sulfonamide conditions, where the sodio-N-chlorosulfonamide salts could be used directly with either the t-butanol or chloroform/water - phase transfer catalyst procedures (Sharpless et al. J. Org. Chem. 1978, 43, 2544).

The addition of nucleophiles such as tetraethylammonium acetate were also proven to be beneficial to the reaction in the procedures using the silver and mercury salts of the chloramines from carbonates. Alternatively, the reactivity and yields were enhanced by addition of excess $AgNO_3$ and $Hg(NO_3)_2$ (over that needed to react with the NaClNCOOR salt) Sharpless et al. J. Org Chem. 1980, 45, 2710.

Preferred conditions included employment of $ROCONClNa+Hg(NO_3)_2+Et_4NOAc$ with N-chloro-N-sodiocarbamates; these conditions were recommended as the best procedure for mono, di and tri substituted olefins even including some olefins unreactive in all of the various chloramine T based processes. (Sharpless et al. Org. Syn. 1981, 61, 93).

Among the carbamates tried, it was found that both benzyl N-chloro-N-argentocarbamate and tert-butyl N-chloro-N-argentocarbamates (or mercurio analogs) were among the most effective oxidants, especially with addition of nucleophiles such as tetraethylammonium acetate. Other carbamates such as isopropyl, ethyl, menthyl and bornyl derivatives were also used, however, chemo, regio and stereoselectivities were lower. Virtually no asymmetric induction was observed when chiral menthyl or bornyl derived carbamates were employed for hydroxyaminations. (Sharpless et al J. Am. Chem. Soc. 1978 100, 3596).

Sharpless disclosed the use of stoiciometric amounts of a first generation monovalent alkaloid ligand with a tert-butyl derived N-chloro-N-argentocarbamate for hydroxyamination in a series of patent applications directed to ligand accelerated catalytic asymmetric dihydroxylation. These disclosures illustrated an hydroxyamination on trans-stilbene with the use of 1.0 equivalent (stoichiometric to olefin) of monovalent DHQD-p-chlorobenzoate (DHQD= hydroquinidine) ligand, 1 mol % osmium tetroxide, silver nitrate (figure) or mercuric chloride (0.80 equivalents; in protocal), 0.09 Molar acetonitrile (93.11 volume % acetonitrile)/water mix (6.89 volume % water) and tertbutyl derived N-chloro-N-argentocarbamate (1.45 equivalents) at 20 EC (figure) or 60 EC (protocal) for 1 hour. The disclosure reported a 51% ee with a 93% yield of aminoalcohol. (Sharpless et al. U.S. Pat. Nos. 4,871,855; 4,965,364; 5,126,494; EP 0 395 729).

In a review on ligand accelerated catalysis, Sharpless et al. noted that a 92% ee had been achieved in a stoichiometric reaction of trioxo-(tert-butylimido) osmium with stilbene in the presence of DHQD-CLB at ambient temperatures (Sharpless et al. Angew. Chem. Int. Ed. Engl. 1995, 34, 1059, ref. 80 "unpublished results"); this mention did not disclose reaction conditions.

Recently, an oxyamination reaction for the hemisynthesis of taxol and analogs was reported using a tertbutyl derived N-chloro-N-argentocarbamate, excess silver nitrate or other metallic salts, with the use of either catalytic or stoichiometric amounts of osmium and the addition of stoichiometric amounts of monovalent DHQD (hydroquinidine), DHQ (hydroquinine) ligands in an unsuccessful attempt to influence the diastereoselectivity and the regioselectivity of the aminohydroxylation process. Solvent conditions varied from acetonitrile, toluene or pyridine, and the reactions were carried out at 4 EC to room temperature, in the dark. The study reported that quinuclidine ligands had no effect on the amino alcohol yields but found that the addition of chiral tertiary amines had some beneficial effect on the yields of the various amino alcohol isomers formed. (Mangatal et al. Tetrahedron 1989 45, 4177). However, the two pseudoenantiomeric alkaloid ligands (i.e. DHQ-OAc and DHQD-OAc; OAc=acetate) gave a mixture of stereo and regioisomeric products. The result indicates that this particular hydroxyamination process (be it stoichiometric or catalytic was unclear) had exhibited no "asymmetric" effects. The procedure can therefore not be regarded as an asymmetric aminohydroxylation.

As a whole, the prior art uses hydroxycarbamates which always run at room temperature with either argento or mercurio salt analogs, monovalent ligands, stoichiometric or catalytic osmium species and organic solvents with trace amounts of water. (Sharpless et al. J. Am. Chem. Soc. 1978, 100, 3596; Sharpless et al. J. Org. Chem. 1980, 45, 2710; Sharpless et al. U.S. Pat. Nos. 4,871,855; 4,965,364; 5,126, 494; EP 0 395 729).

Cleavages of the hydroxycarbamates, to free aminoalcohols, are well known in the art and include mild acid or base hydrolysis and catalytic hydrogenolysis, depending on the attached functionality to the carbamate. (Greene, *Protective Groups in Organic Synthesis*, 1981, Wiley, 1st edn. pp. 223–249).

What is needed is an improved method for catalyzing the asymmetric aminohydroxylation of olefins using carbamate oxidants, wherein the improvement enhances the yields, enantiomeric efficiency, and the regio-selectivity while reducing material and labor costs.

SUMMARY OF THE INVENTION

The invention is directed to an improved method for converting olefinic substrates to asymmetric β-hydroxycarbamate products. The method of the invention employs an asymmetric addition reactions involving the asymmetric addition of an carbamoyl radical and a hydroxyl radical to the olefinic substrate. Enhanced yields, regioselectivity, and enantioselectivity may be achieved according to the method of the invention. The asymmetric addition reaction is carried out in a reaction solution which includes the olefinic substrate, an osmium catalyst, a chiral ligand for enantiomerically and regioselectively directing the asymmetric addition, a carbamate, and a solvent or co-solvent. The carbamate serves as a source for the carbamoyl radical. The olefinic substrate and carbamate are present and soluble within the solvent or cosolvent in stoichiometric amounts. The osmium is present within the solvent or co-solvent in catalytic amounts.

One aspect of the invention is directed to the use of reaction solutions which employ solvents or co-solvents having both an organic component and an aqueous component, the aqueous component constituting 10% or more of the reaction solution on a volume basis. Reaction solutions containing 50% water by volume are preferred because peak yields and/or peak enantiomeric efficiencies are shown to be achieved with this mixture of solvents. Preferred organic components of the solvent or co-solvent include acetonitrile, tert-butanol, and n-propanol.

Another aspect of the invention is directed to the use of only catalytic amounts of both the osmium catalyst and the chiral ligand in connection with the asymmetric β-aminohydroxylation reaction. The operable concentration range for the osmium catalyst in the reaction solution is between 0.5 mole % and 20 mole %. The preferred concentration of the osmium is within a range of 2–4 mole %. The operable concentration range for the chiral ligand in the reaction solution is n within a range of substantially 1 mole % to 10 mole %. The preferred concentration of the osmium is approximately mole 5 mole %.

Another aspect of the invention is directed to the above methods for converting an olefinic substrate to an asymmetric β-hydroxycarbamate product by asymmetric addition as described above wherein the solvent including an aqueous component of at least 10% or greater on a volume basis; and the solvent substantially lacks an ancillary metal salt. Specific ancillary metal salts which should be excluded are silver salts and mercury salts.

DESCRIPTION OF FIGURES

FIG. 2 shows the olefin substrate, hydroxy-carbamate product, % ee (enantioselectivity) with the $(DHQ)_2PHAL$ (DHQ=hydroquinine; PHAL=phthalazine) or $(DHQD)_2PHAL$ (DHQD=hydroquinidine) ligands, % yields and time (h).

FIG. 16 shows the olefin substrate, hydroxy-carbamate product, % ee (enantioselectivity) with the (DHQ)$_2$PHAL (DHQ=hydroquinine; PHAL=phthalazine) or (DHQD)$_2$PHAL (DHQD=hydroquinidine) ligands, % yields and time (h).

FIG. 23 shows the olefin substrate, hydroxy-carbamate product, % ee (enantioselectivity) with the (DHQ)$_2$PHAL (DHQ=hydroquinine; PHAL=phthalazine) or (DHQD)$_2$PHAL (DHQD=hydroquinidine) ligands, % yields and time (h).

FIG. 24 shows the olefin substrate, hydroxy-carbamate product, % ee (enantioselectivity) with the (DHQ)$_2$PHAL (DHQ=hydroquinine; PHAL=phthalazine) or (DHQD)$_2$PHAL (DHQD=hydroquinidine) ligands, % yields and time (h).

FIG. 26 shows the olefin substrate, hydroxy-carbamate product, % ee (enantioselectivity) with the (DHQ)$_2$PHAL (DHQ=hydroquinine; PHAL=phthalazine) or (DHQD)$_2$PHAL (DHQD=hydroquinidine) ligands, % yields and time (h).

I. Olefin Classes

Figure 1:
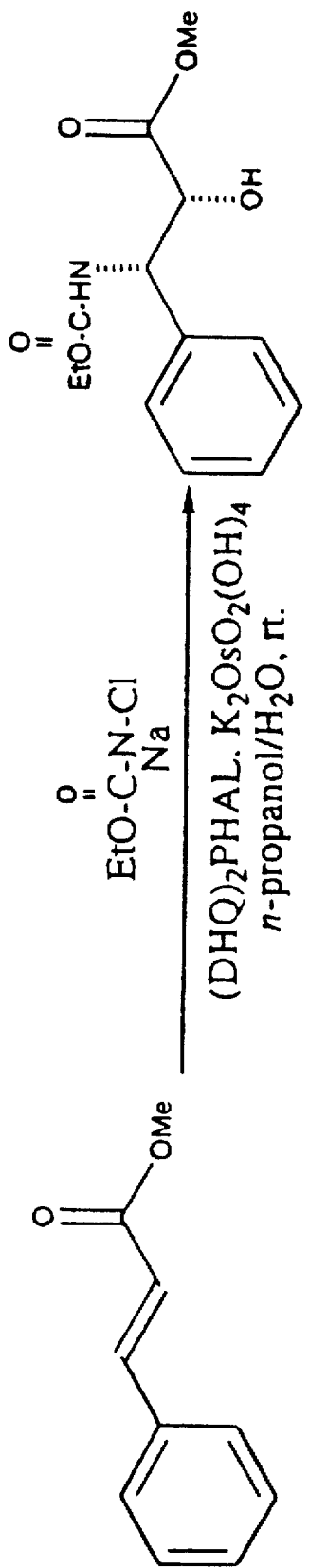
FIG. 1 illustrates the asymmetric aminohydroxylation of methylcinnamate to its corresponding α-hydroxy-β-ethylcarbamate.
Figure 3:
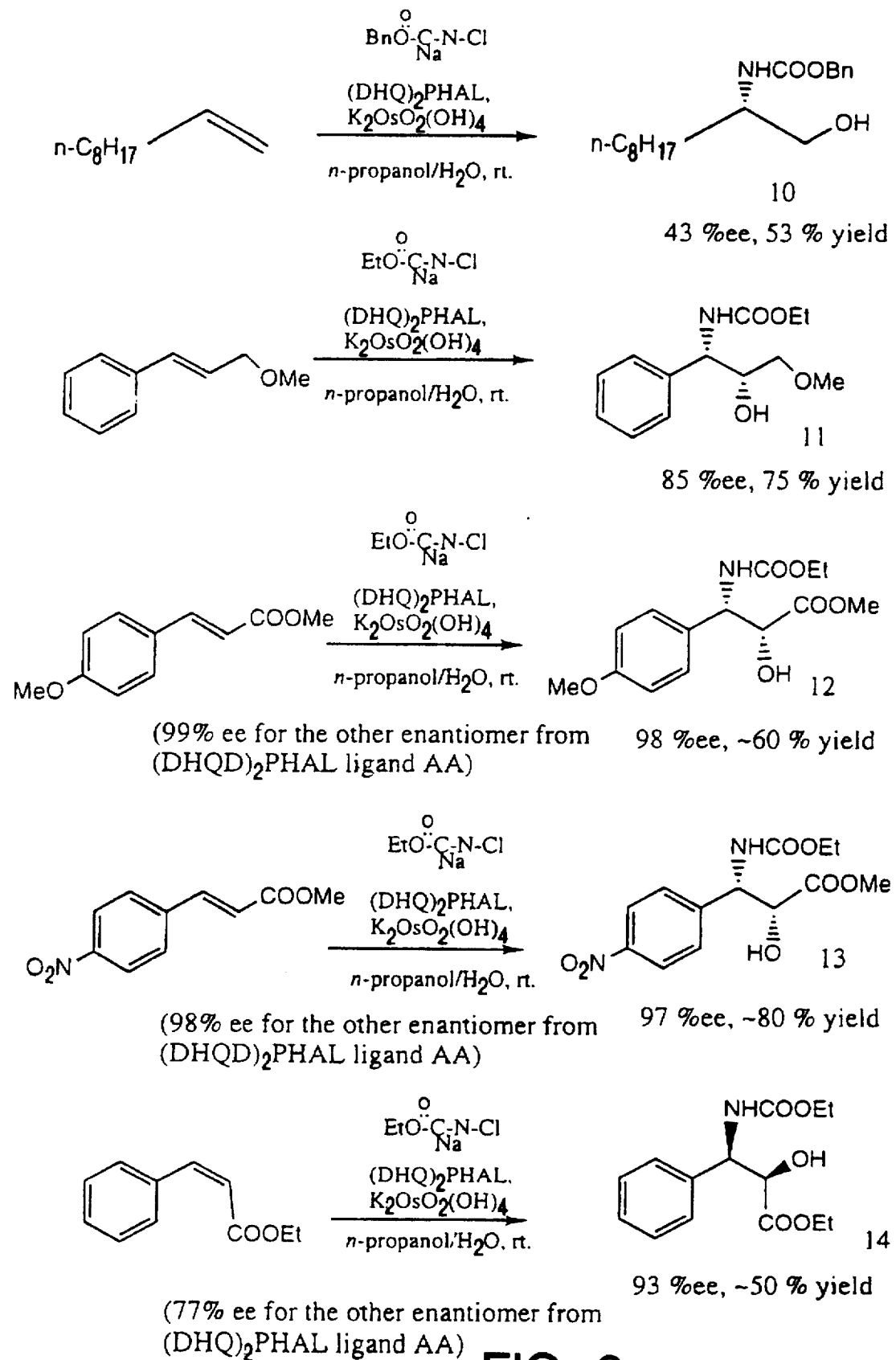
FIG. 3 illustrates conversion of a variety of olefins with noted conditions, yields and % ee.
Figure 4:
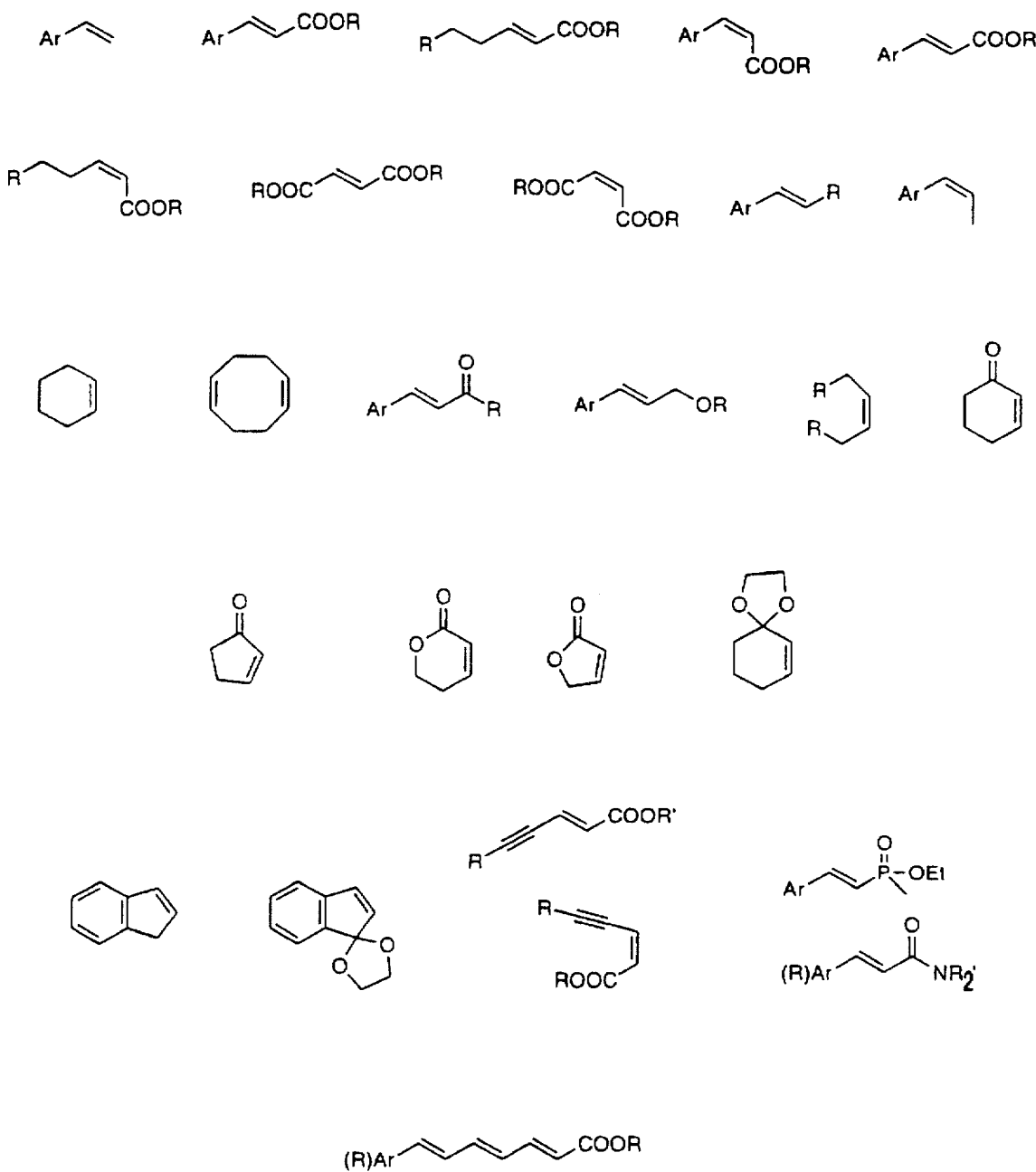
FIG. 4 shows a series of preferred substrate olefins where R=hydrogen, aromatic, alkyl, heterocycles, hydroxyl substituents, esters, ethers, as appropriate for substrate.
Figure 5:
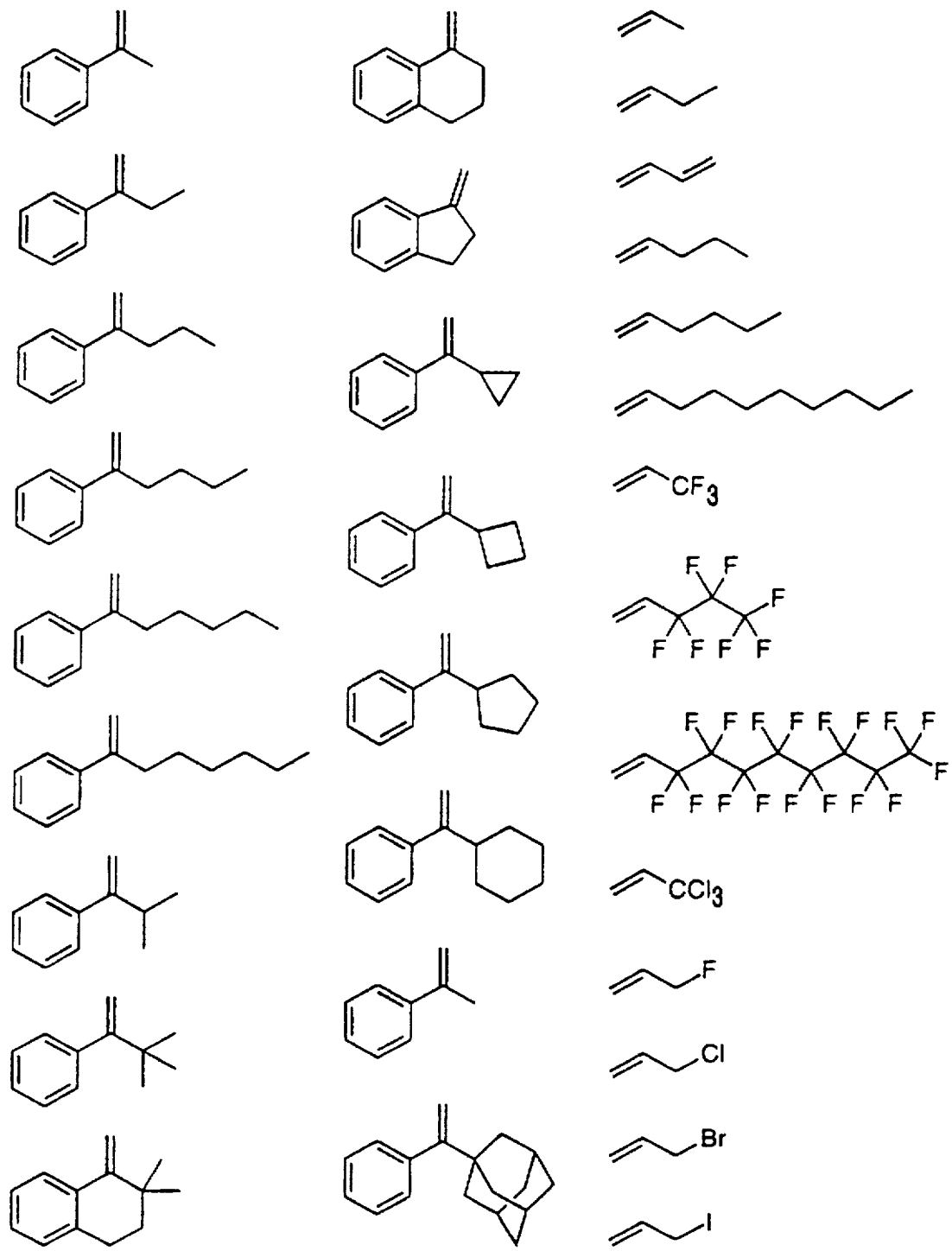
FIG. 5 illustrates a series of compatible olefins for aminohydroxylation including some 1,1 disubstituted and monosubstituted olefins with various functionalities.
Figure 6:
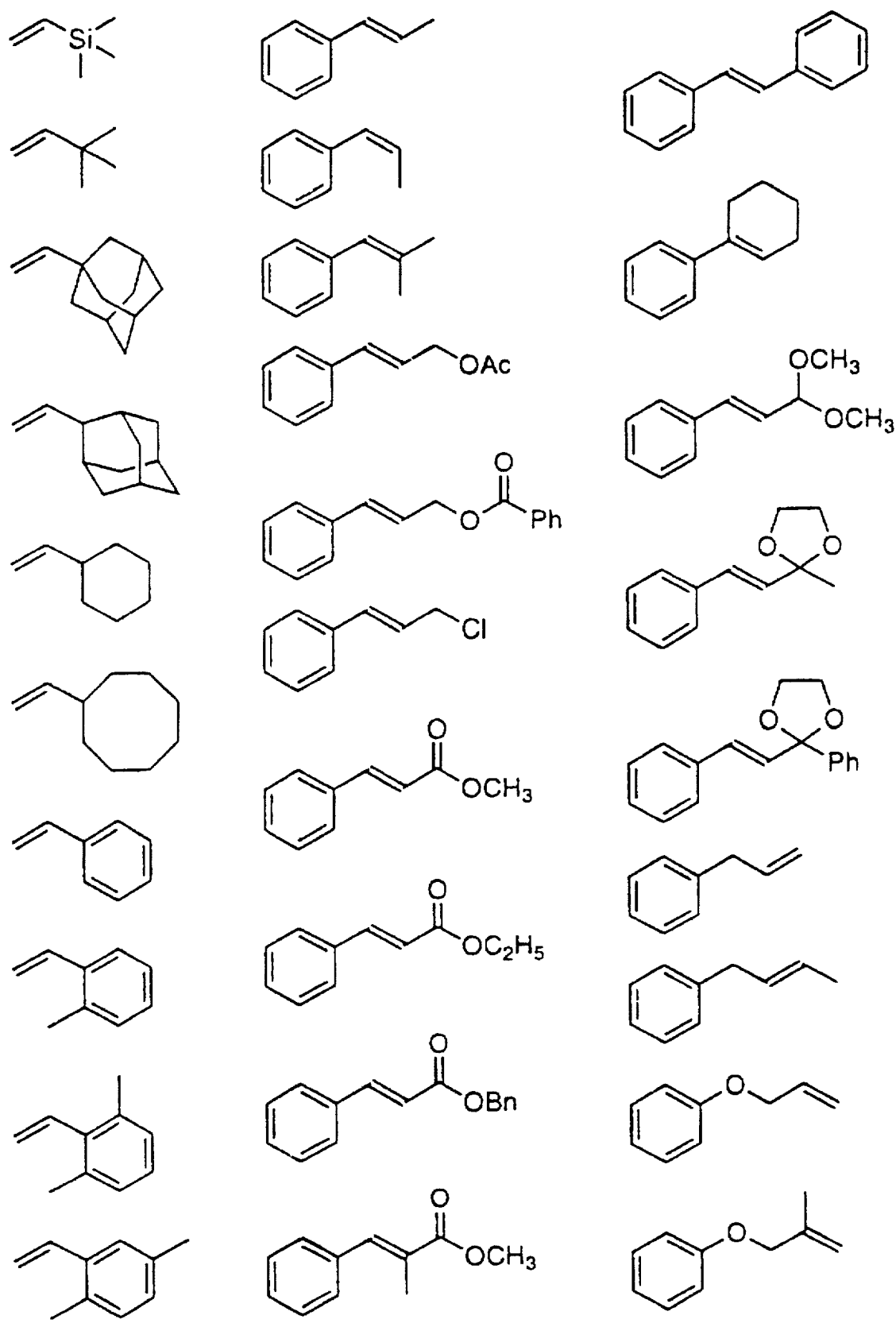
FIG. 6 illustrates a series of compatible olefins for aminohydroxylation including some monosubstituted and disubstituted olefins (cis and trans) with various functionalities.
Figure 7:
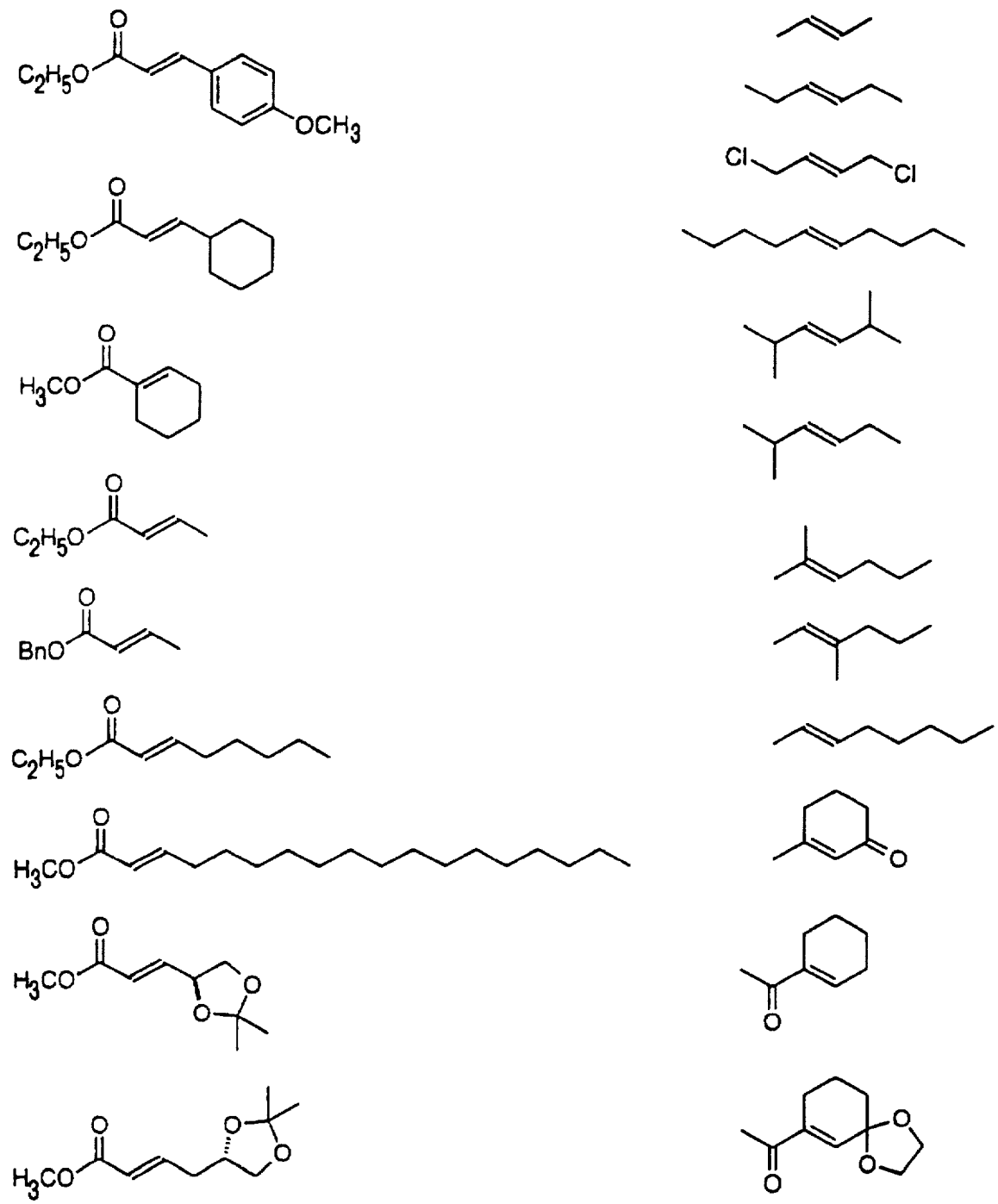
FIG. 7 illustrates a series of disubstituted olefins for asymmetric aminohydroxylation with various functionalities.
Figure 8:
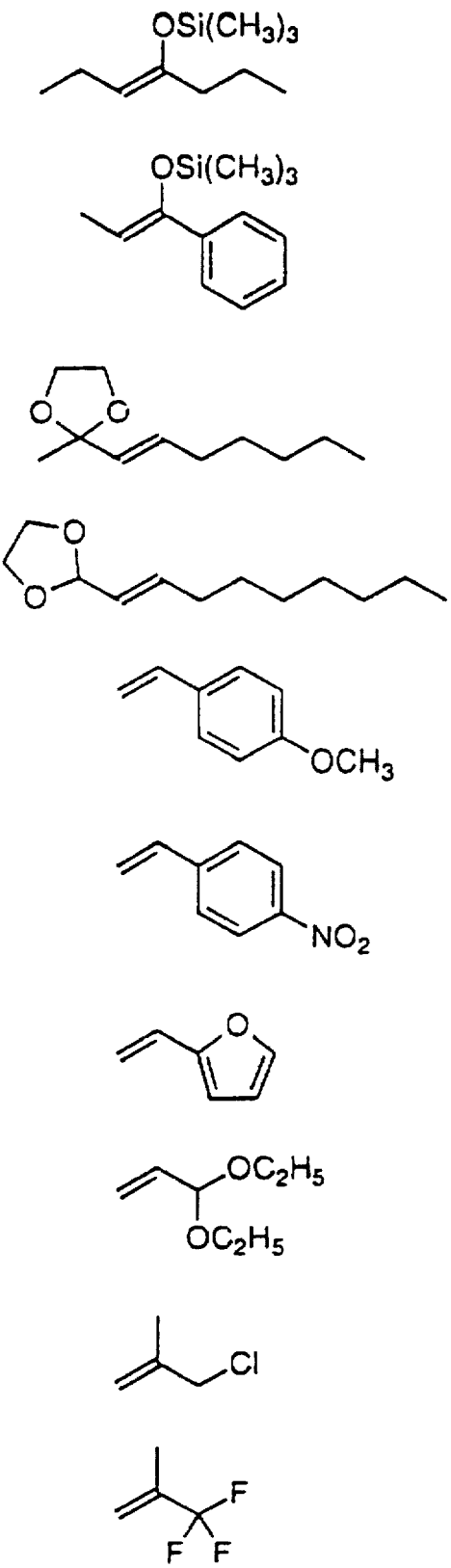
FIG. 8 illustrates a series of monosubstituted and disubstituted olefins for aminohydroxylation with various functionalities.
Figure 9:
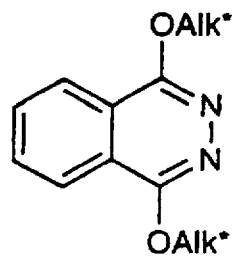
FIG. 9 illustrates the preferred ligand classes for aminohydroxylation wherein PHAL=Phalazine; DP-PHAL= diphenyl-phthalazine; DPP=diphenyl pyrazinopyridazine; PYR=pyrimidine; IND=indoline; AQN=anthraquinone; dihydroquinidyl (DHQD) and dihydroquinyl (DHQ).
Figure 9:
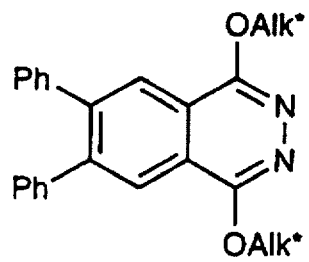
Figure 9:
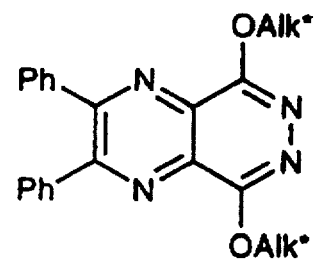
Figure 9:
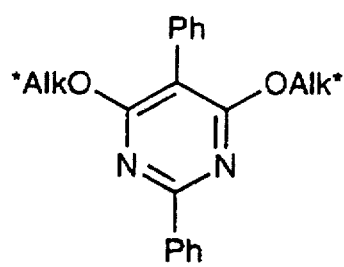
Figure 9:
Figure 9:
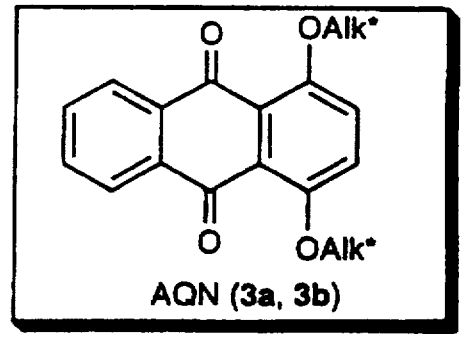
Figure 9:
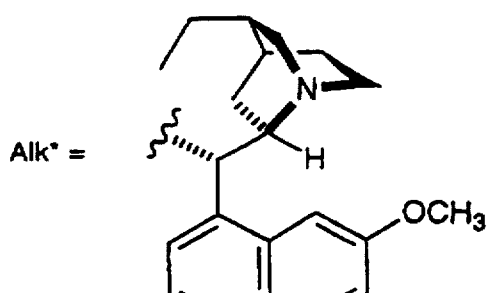
Figure 9:
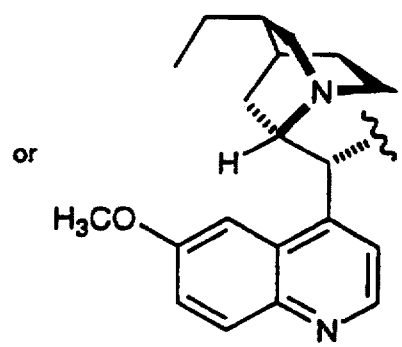
Figure 10:
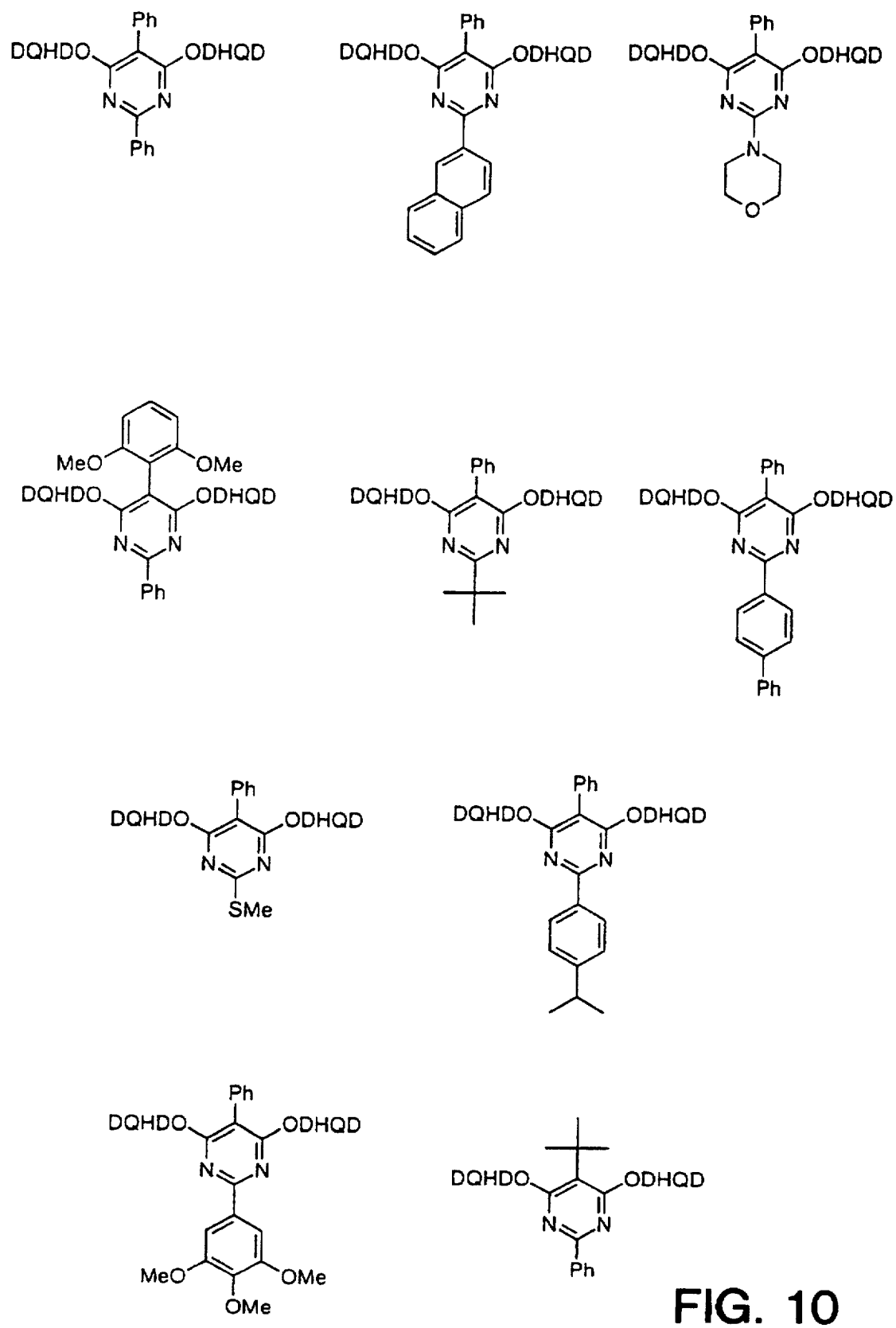
FIG. 10 illustrates additional ligands compatible for the asymmetric aminohydroxylation reaction.

The asymmetric aminohydroxylation (AA) works well with three olefin classes: 1) monosubstituted i (table 1); 2) cis-disubstituted iii (table 1), and 3) trans-disubstituted iv olefins. The 1,1 disubstituted ii and trisubstituted types of olefins give only racemic or low ee's while the tetrasusbstituted class, vi, does not provide any signs of turnover.

TABLE I

| olefin class | i | ii | iii | iv | v | vi |
|---|---|---|---|---|---|---|
| AD ee range | good 30–99% | good 70–99% | poor 20–80% | excellent 90->99.8% | excellent 90–99% | variable 20–97% |
| AA ee range | good Ar, 80–99% R, 40–80% | ? | good | excellent up to 99% | ? | ? |

II. Regioselectivity

High regioselectivity is one of the more useful features of the AA. The carbamate-version exhibits a strong preference for nitrogen attachment to the olefinic carbon bearing an aromatic substituent or, in the case of olefins conjugated with a strong electron withdrawing group (EWG), the nitrogen is strongly directed to the olefinic carbon distal to the EWG as illustrated in Scheme I. The alkaloid ligand is responsible for high regioselectivity. When the ligand is omitted, there is little preference for either regioisomer.

Beyond probable contributions from "binding pocket" effects, the strong regioselection phenomenon requires the operation of powerful electronic determinants.

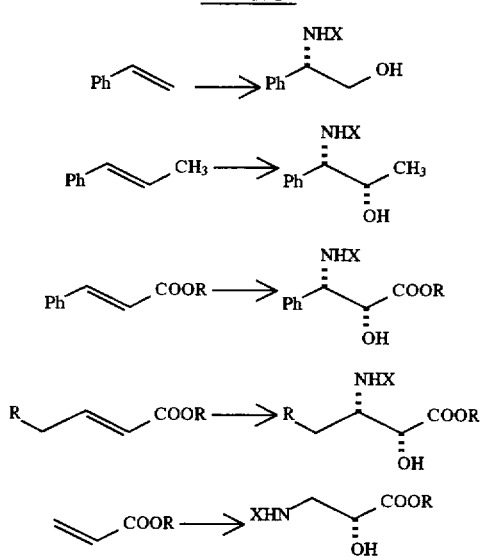

Scheme I.

III. Mechanistic Hypothesis (1) The Os=N—X linkage should be more polarized (especially when X is electron withdrawing) and also more reactive than the Os=O linkage. The Os=N—X linkage, therefore, reacts preferentially with the olefin to give osmaazetidine intermediates wherein the olefin osmium complexes have been omitted for clarity (Scheme II).

(2) Unsymmetric olefins such as cinnamate should strongly bias the insertion process favoring osmaazetidine 1i over its regioisomer 2i. Yet in the absence of a ligand roughly equal amounts of the regioisomeric products 1p and 2p (derived from 1i and 2i, respectively) are produced. This is not surprising since one might predict that the much weaker Os—C bond in 2i (c.f. same bond in 1i) could easily siphon much of the reaction through intermediate 2i (i.e. 2i to 2p) even if the concentration of 1i were a 1000 times greater (Scheme II).

(3) Intervention by the chiral ligand can dramatically change the outcome (Scheme III). The "binding pocket" effect favors formation of ligated intermediate 1i'. In addition, rearrangement of the strong Os—C bond in 1i' (c.f. EWG effect on M—C bond strengths) to product 1p' is facilitated by both steric and orbital-electronic effects mediated by the ligand. In this way the factors which had destroyed regioselectivity in the absence of the ligand are overridden, and the reaction is channeled along a single path at each point of decision: (1) 3-aza or 2-aza product; and (2) S,R- or R,S-enantiomer. Here the ligand controls both the regio- and the enantioselectivity.

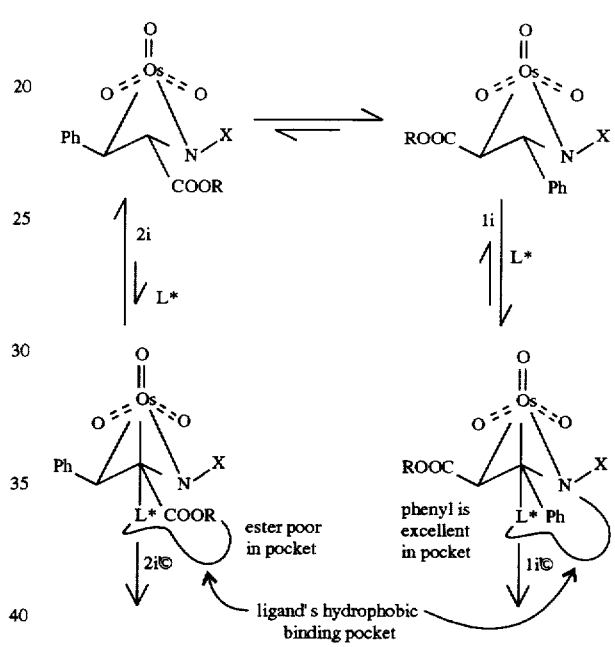

Scheme III.

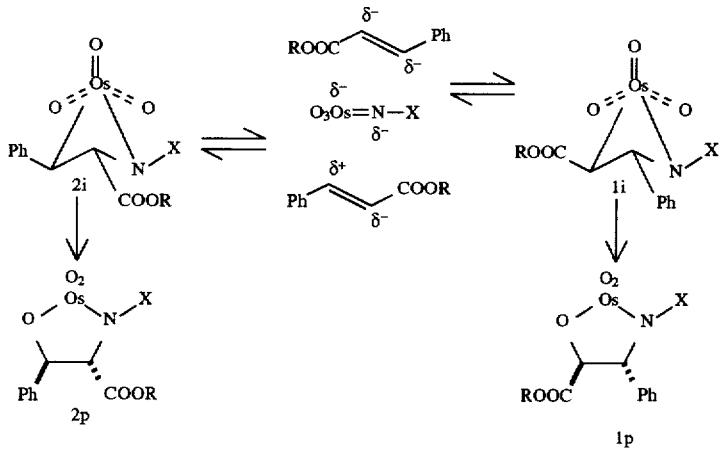

Scheme II.

-continued
Scheme III.

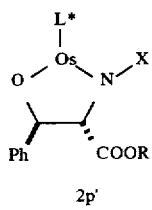

2p'

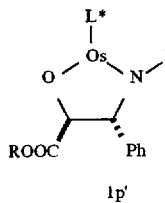

1p'

IV Rationale for Olefin Preferences

Figure 29:
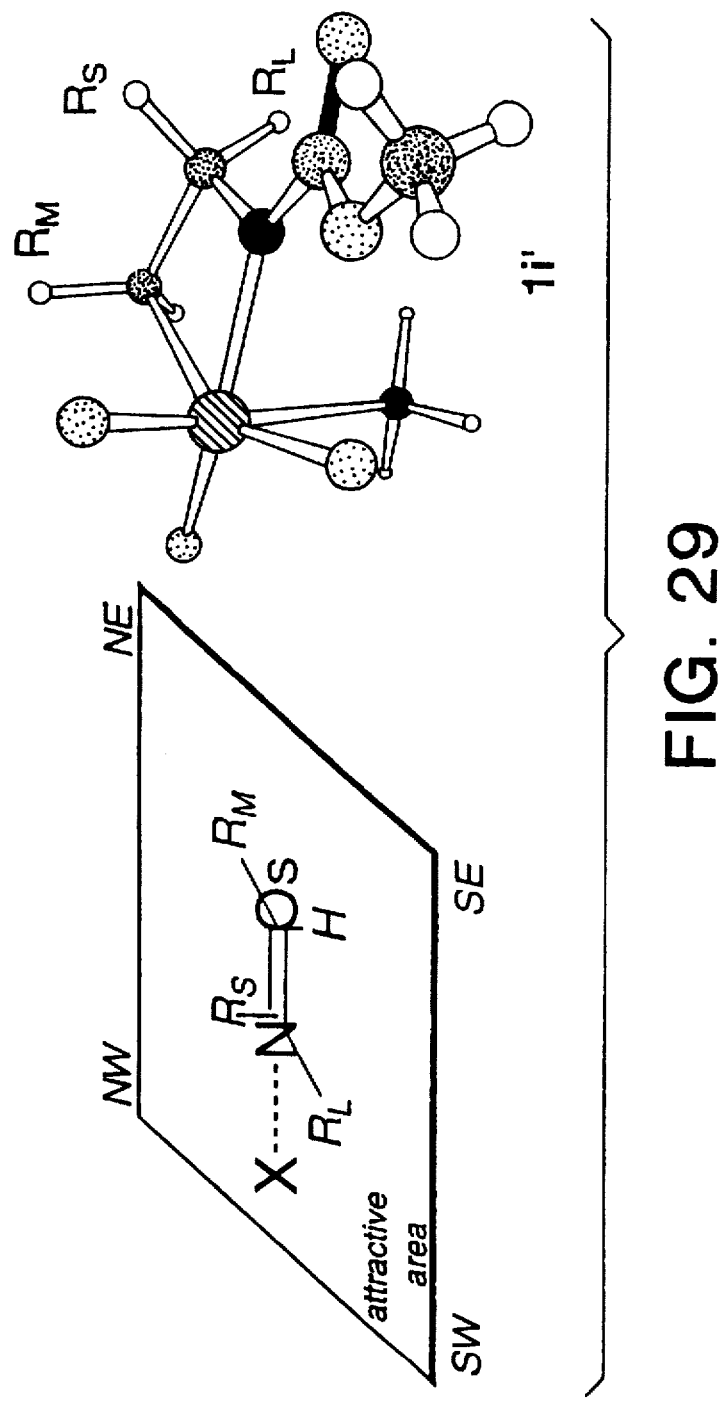
FIG. 29 illustrates a quadrant mnemonic for the key ligated osmaazetdine intermediate 1i' of the AA reaction.

A quadrant mnemonic for the key ligated osmaazetdine intermediate 1i' (FIG. 29) provides an explanation as to why only 3 of the 6 olefin classes appear to make good AA substrates. Three of the four quadrants are fairly easy to assign and to fit to the 3D-picture of the ligated osmaazetidine intermediate (FIG. 29): (1) the NE. quadrant can handle a large group, it corresponds to the pseudo-equatorial substituent ($R_M$) on the carbon bound to osmium; (2) the SE. quadrant is the one that presents as most crowded, supposedly due to the pseudoaxial substituent on the carbon bond to osmium which is very close to the ligand at its point of ligation to osmium (unless it is a hydrogen atom, things rarely go well in the AD or the AA); (3) the SW. quadrant, as in the AD, gives every sign of possessing a good "binding pocket" for aryl and some alkyl substituents ($R_L$). As before, the situation in the NW. quadrant is less predictable. This quadrant encompasses the pseudoaxial substituent ($R_S$) bound to oxygen (AD) or nitrogen (AA) which in either case is close to the oxo group on osmium which is trans to the ligating nitrogen of the ligand. Hydrogen bonding groups in this position often have a positive effect on both the rates and the enantioselectivities of the AD reaction (Sharpless et al Chem Rev., 1994, 2488).

V. Rationale for Incompatibility With Some Olefin Classes

A difference between the AA and the AD, which has important practical implications, is the loss of two major olefin classes for the AA. (The tetrasubstituted class vi, is ignored here since it is theleast available class of olefins and has not been shown towork with the AA process). These are the 1,1-di- and trisubstituted classes (ii and v in the Table) which are generally very good in the AD. (Recall that so far the PHAL ligands have been used almost exclusively in our AA studies so these comparisons seem merited). Most attempted AA's on 1,1-di- and trisubstituted olefins (ii and v, Table) have failed to give enantiomerically enriched products, although excellent yields of racemic aminohydroxylation products have occasionally resulted.

What is the problem for the AA with these substitution patterns? In both cases a hydrogen substituent can be placed in the crucial SE. quadrant. The stand-out difference between the AA and AD suggests a possible answer. The AA bears an extra substituent, the one on nitrogen, and most importantly, in the key intermediates this substituent is forced to be "in close," a consequence of the great reactivity of the Os=N— group to which it is attached. In our usual quadrant analysis this "new" substituent must find a place for itself in a region which is crowded by parts of the ligand and by substituents (originating from the olefin) on the osmaazetidine.

In the ligated osmaazetidine intermediate (FIG. 29) this nitrogen substituent lies roughly due West at the boundary of the NW. and SW. quadrants. In spite of negotiable open space in the "up/down direction" the nitrogen substituent could perturb the entire system, especially for olefins with substituents in both the NW. and SW. sectors. Any perturbing effects of the imido nitrogen substituent should diminish as it becomes smaller, and this prediction is dramatically born out by the results using smaller sulfonamides (e.g. $CH_3SO_2NH_2$) and the carbamates, which are inherently much smaller than any sulfonamide near the crucial point of attachment to nitrogen.

A reason that the AA process is poor for 1,1-di- and trisubstituted olefins is due to the fact that the Os=N— group reacts first forcing the ligand to bind to the osmaazetidine, which has a hydrogen in the SW. quadrant. The relevant intermediates are A and B respectively:

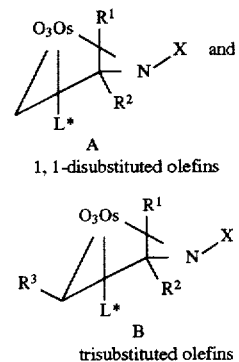

A
1, 1-disubstituted olefins trisubstituted olefins
B

In either case, the nitrogen is forced to end up attached to a disubstituted carbon. The substituent on the nitrogen may destabilize the resulting ligated osmaazetidine intermediates A and B in a manner which does not occur for the analogous ligated osmaoxetanes.

While olefin classes ii and v may never enter the useful range in these AA processes, one can imagine using the electronic and binding pocket effects to create "ideal" substrates even for difficult classes, e.g.:

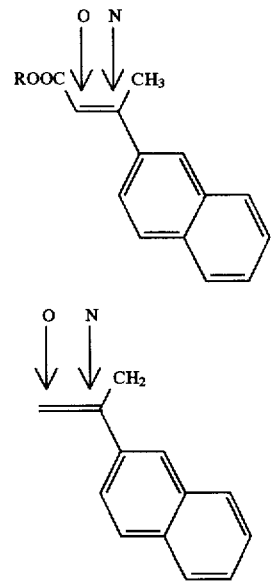

In light of the above speculations, one might wonder why the cis-disubstituted olefins (iii) represent a successful class in the AA. These olefins are also forced to have a substituent in the NW. quadrant. However, now there is only one substituent on the carbon bound to nitrogen in the key intermediate related to B (i.e. $R_2$=H). This will increase the conformational flexibility of the intermediate making cis-disubstituted olefins good candidates for the AA process.

Synthetic Protocols

NMR spectra were recorded on Bruker AMX-500, AM-300, or AM-250 instruments. The following abbreviations were used to explain the multiplicities: s, singlet; d, doublet; t, triplet; q, quartet; m, multiplet; apt, apparent; b, broad; obs, obscured. IR spectra were recorded on Nicolet 205, Perkin Elmer 1600 or Galaxy 2020 series FT-IR spectrophotometers. Optical rotations were recorded using a Perkin Elmer 241 polarimeter. High-resolution mass spectra (HRMS) were recorded on a VG ZAB-ZSE mass spectrometer under Fast Atom Bombardment (FAB) conditions, at the Scripps Research Institute.

All reactions were monitored by color change, HPLC, GC or thin-layer chromatography carried out on 0.25 mm Whatman silica gel plates (K6F-60 Å) using UV light, p-anisaldehyde, or 7% ethanolic phosphomolybdic acid and heat as developing agent. E. Merck silica gel (60, particle size 0.040–0.063 mm) was used for flash column chromatography. Tetrahydrofuran (THF) and ethyl ether were distilled from sodium-benzophenone and methylene chloride, benzene and toluene were distilled from calcium hydride. All reagents were obtained from Aldrich Chemical Co. Inc. unless otherwise noted. Solvents used for workup, chromatography, and recrystallizations were reagent grade from Fisher Scientific and were used as received.

Chloramine Sodium Salt Preparation

Procedure as adapted from Campbell et al. *Chem. Rev.*, 1978, 78, 65.

General Asymmetric Aminohydroxylation Conditions:

To a solution of NaOH (3.05 equivalents) in 0.13 Molar equivalent of water to olefin is added desired carbamate (3.10 equivalents). The resulting solution is stirred at room temperature for 10 min and then t-butyl hypochlorite (3.05 equivalents; Aldrich Chemical) is added dropwise. The above solution is stirred for another 10 min and then 0.13 Molar equivalent of n-propanol (t-butanol or acetonitrile can be substituted) and $(DHQ)_2$-PHAL (0.05 equivalents, 5 mol %; $DHQD_2$-PHAL obtains antipode) are added to form a homogeneous solution. The reaction mixture is immersed in a room temperature bath and added substrate olefin (1 equivalents) and $K_2OsO_2(OH)_4$ (0.04 equivalents, 4 mol %) are then added. The reaction is stirred for 45 min with the color changing from light green to light yellow, followed by quenching by addition of aqueous sodium sulfite; the phases are separated, and the aqueous phase was extracted with ethyl acetate. The combined organic extracts are washed with water and brine, dried over $MgSO_4$ and the solvent concentrated to give the crude product. Flash chromatography of this material provides the hydroxycarbamate product.

Solvent Variations:

Preferred solvents include acetonitrile, n-propanol, tert-butanol.

Suitable solvents include methanol, ethanol, n-butanol, n-pentanol, 2-Propanol, 2-Butanol, tert-butanol, ethylene glycol; nitriles: acetonitrile, propionitrile; ethers: tetrahydrofurane, diethyl ether, tert. butyl methyl ether, dimethoxyethane, 1,4-dioxane; miscellaneous: dimethyl formamide, acetone, benzene, toluene, chloroform, methylene chloride.

Percent Water/Organic Solvent Variations

Figure 11:
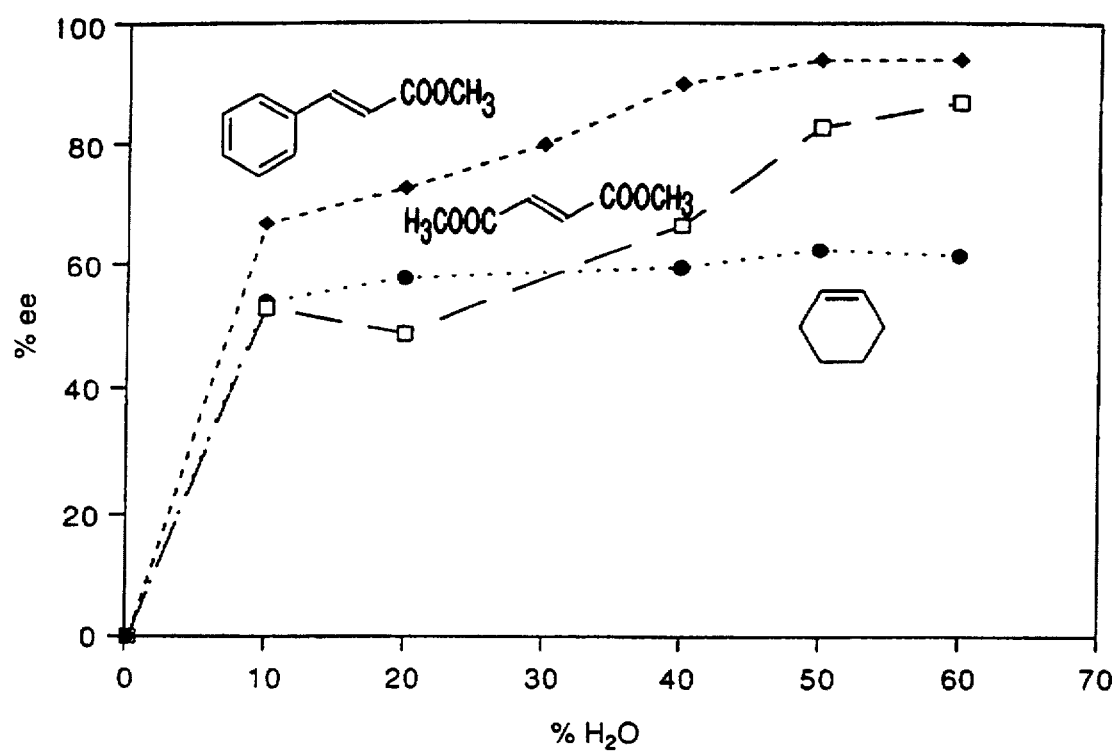
FIG. 11 illustrates the effects of water on the enantioselectivity of the asymmetric aminohydroxylation. The horizontal axis shows % water in increasing organic solvent (right side of graph; solvent used was n-propanol but acetonitrile, tert-butanol can also be used) where 0% water (left side of graph) indicates 100% organic solvent. The vertical axis shows % ee (enantioselectivity). Three substrates are shown including methyl cinnamate (dark diamond - medium dashed line), dimethylfumarate (open box - long dashed line) and cyclohexene (dark circle - short dashed line). No turnover and therefore no enantioselectivity is found at 0% water. Optimal concentration for highest enantioselectivity is approximately 50% water/50% organic solvent but can vary between 10–60% depending on substrate.
Figure 12:
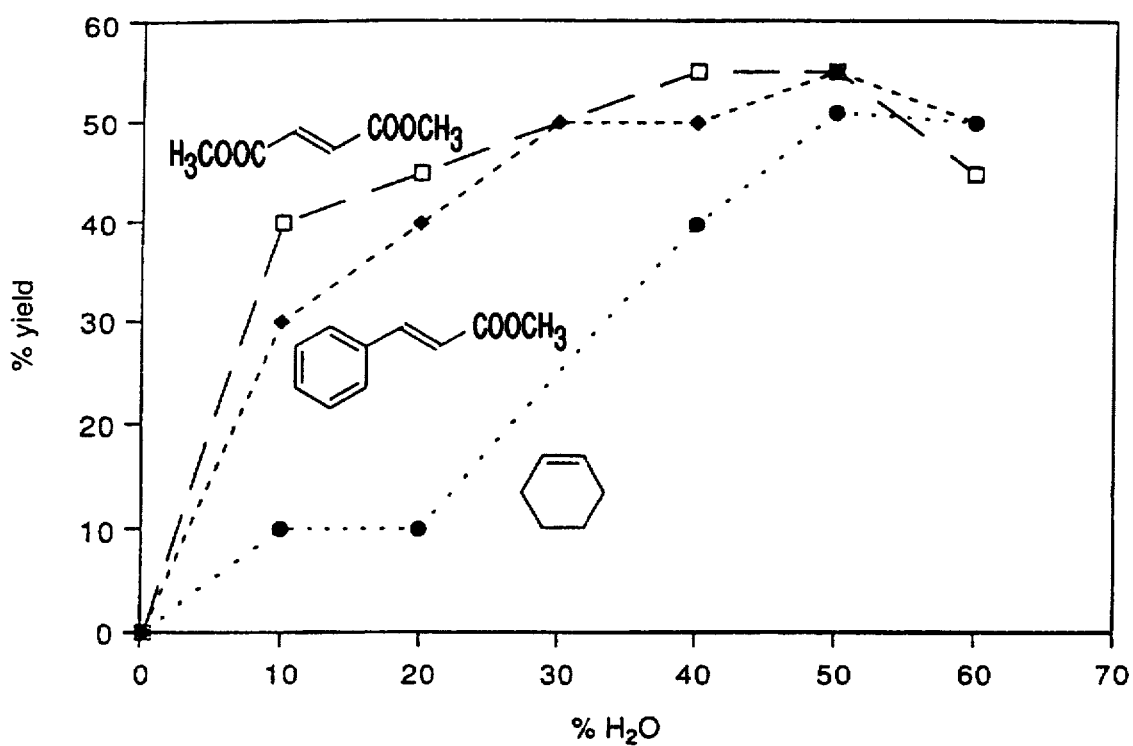
FIG. 12 illustrates the effects of water on the yields of the asymmetric aminohydroxylation. The horizontal axis shows % water in increasing organic solvent (right side of graph; solvent used was n-propanol but acetonitrile, tert-butanol can also be used) where 0% water (left side of graph) indicates 100% organic solvent. The vertical axis shows % yield. Three representative substrates are shown including methyl cinnamate (dark diamond - medium dashed line), dimethylfumarate (open box - long dashed line) and cyclohexene (dark circle - short dashed line). No turnover is found at 0% water. Optimal concentration for highest yield is approximately 50% water/50% organic solvent but can vary between 10–60% depending on substrate.
Figure 13:
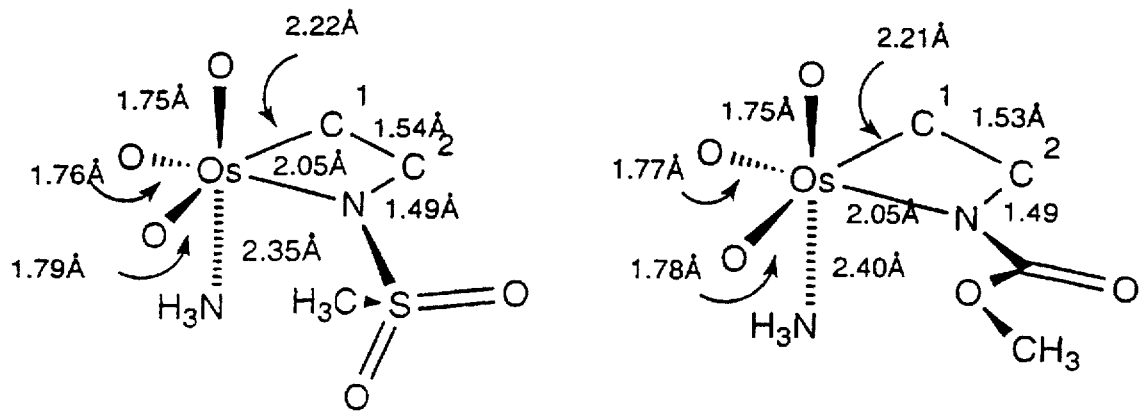
FIG. 13 illustrates a molecular modeling study which was performed on both carbamate and sulfonamide osmium complexes; key intermediates in the catalytic process. The structures of N-methylsulfonyl- and N-methoxycarbonyl osmaazetidines were optimized by density functional theory (DFT) with Becke's three parameter hybrid method using LYP correlation functional (B3LYP). The calculations were performed by using Gaussian 94 program[1] with LanL2DZ basis set. Due to the complexity of the chiral ligands, a simplied model was used. Models of N-methylsulfonyl- and N-methoxycarbonyl- osmaazetidines were adopted where the osmium atom was complexed with ammonia instead of the chiral ligand. The calculations show that the osmaazetidine rings have the flat conformations with no significant puckering as observed in osmaoxetanes. The osmaazetidine nitrogen is slightly pyramidised in the methylsulfonyl case. In the carbamate case, the osmaazetidine nitrogen is planar. The osmaazetidines are possible intermediates in [2+2] mechanistic pathway of the AA. Dihedral and bond angles are indicated.
Figure 14:
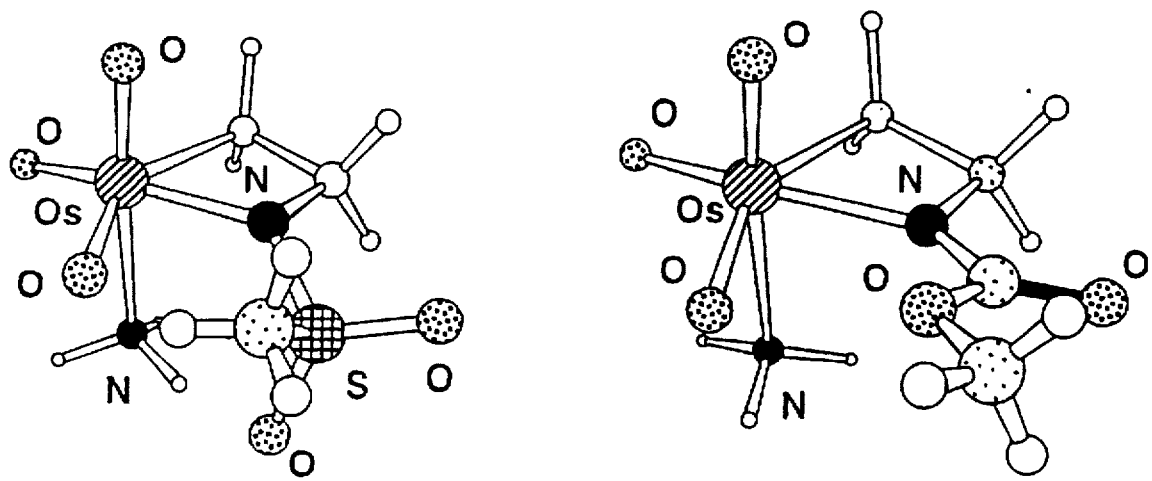
FIG. 14 illustrates a ball and stick view of the molecular modeling study as shown in FIG. 13 and performed on both carbamate and sulfonamide osmium complexes.
Figure 15:
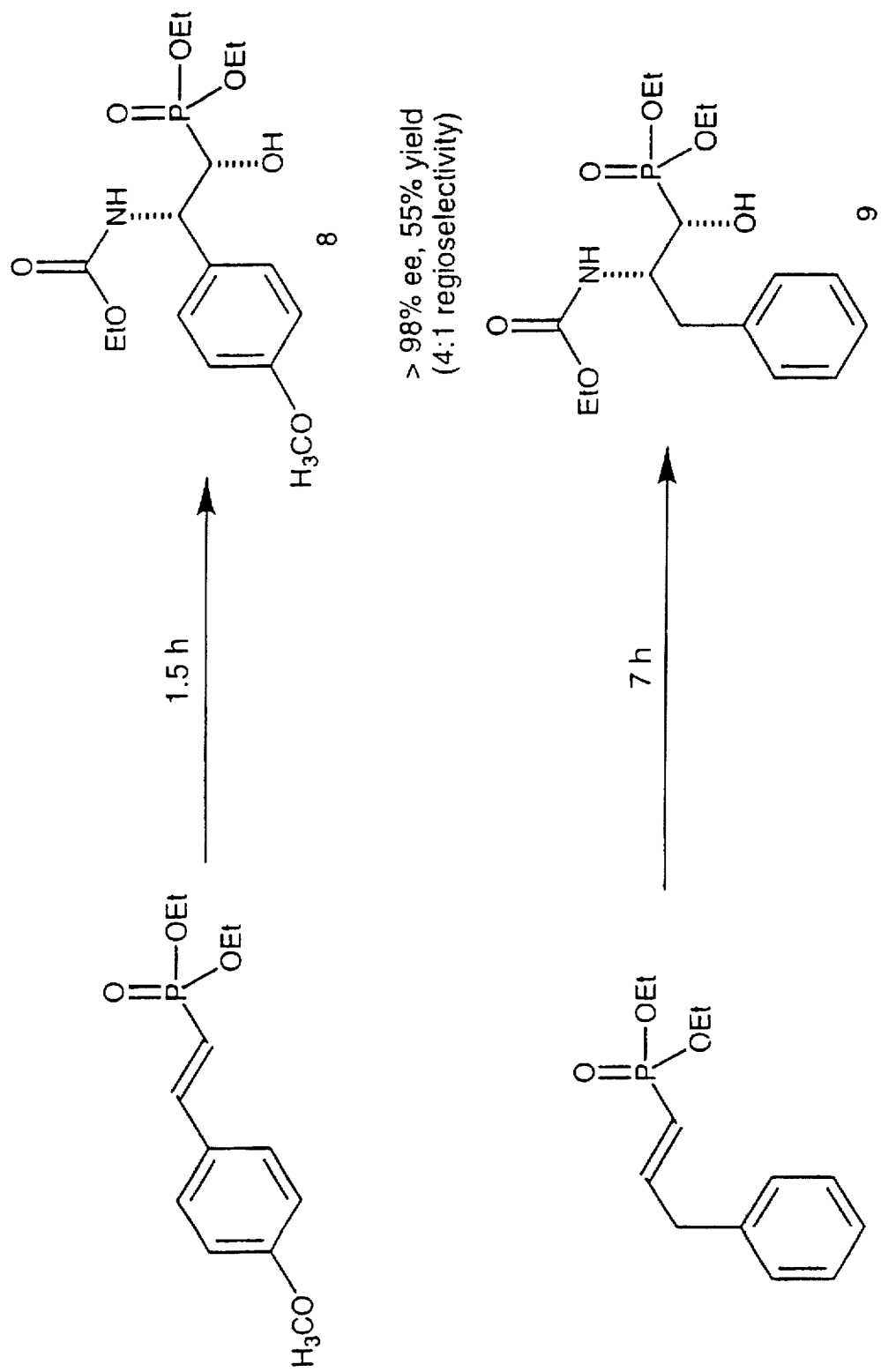
FIG. 15 illustrates the asymmetric aminohydroxylation of aromatic vinyl phosphonate esters to their corresponding hyroxy-carbamate products with ee and yields indicated.
Figure 17:
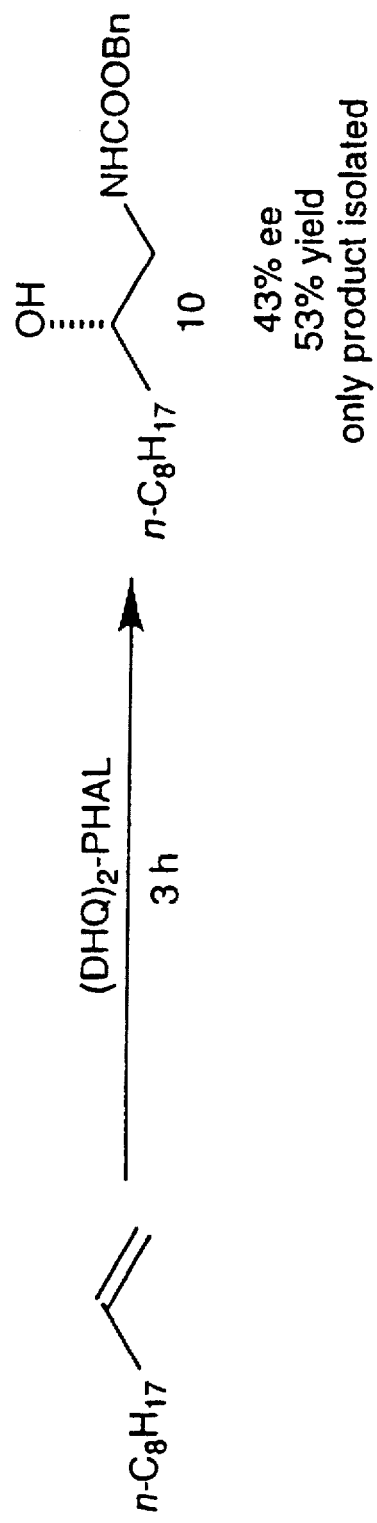
FIG. 17 illustrates the asymmetric aminohydroxylation of n-C$_8$H$_{17}$CHCH$_2$ to the corresponding hydroxy-carbamate product with ee and yields indicated.
Figure 18:
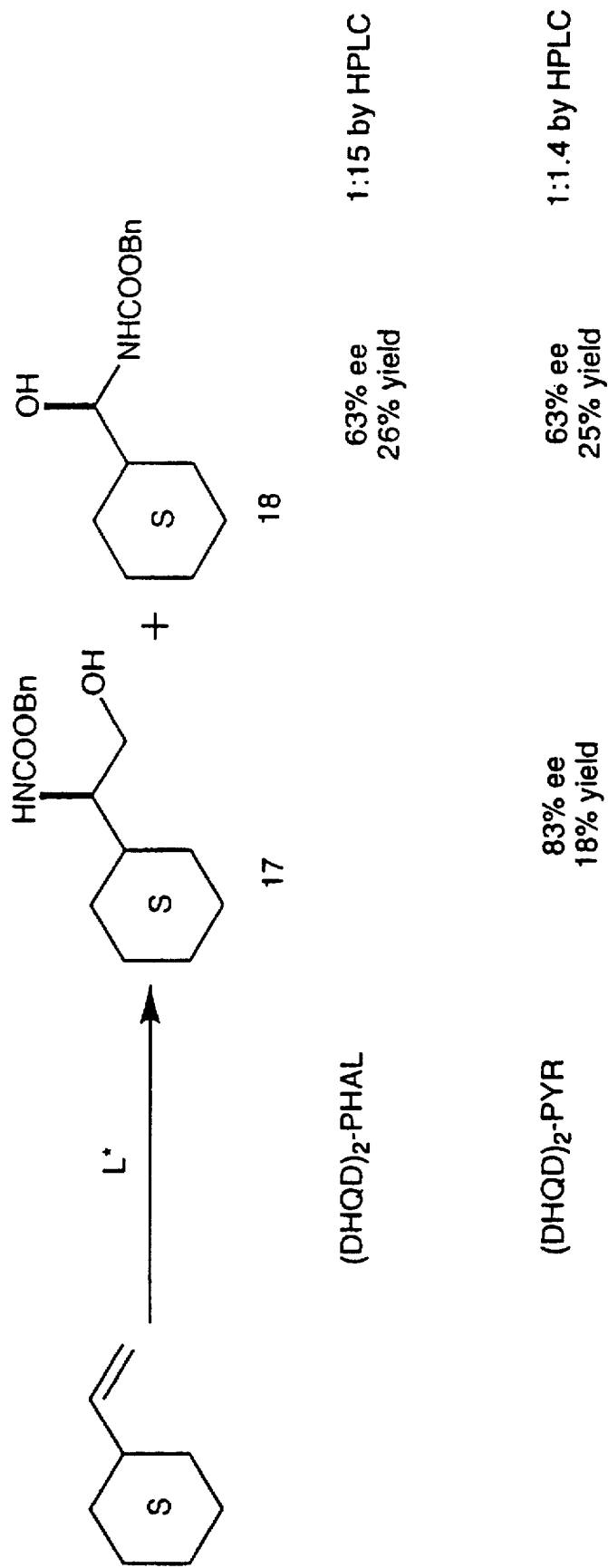
FIG. 18 illustrates the aminoasymmetric conversion of vinyl cyclohexane to the corresponding hydroxy-carbamate product with ee and yields indicated using either (DHQD)$_2$PHAL (DHQD=hydroquinidine; PHAL=phthalazine) or (DHQD)$_2$PYR (DHQD=hydroquinidine; PYR=pyrimidine). The (DHQD)$_2$PYR ligand obtains a 1:1.4 ratio of primary hydroxylated to secondary hydroxylated product (contrast to the (DHQD)$_2$PHAL ligand which obtains a 1:15 ratio primary hydroxylated to secondary hydroxylated product).
Figure 19:
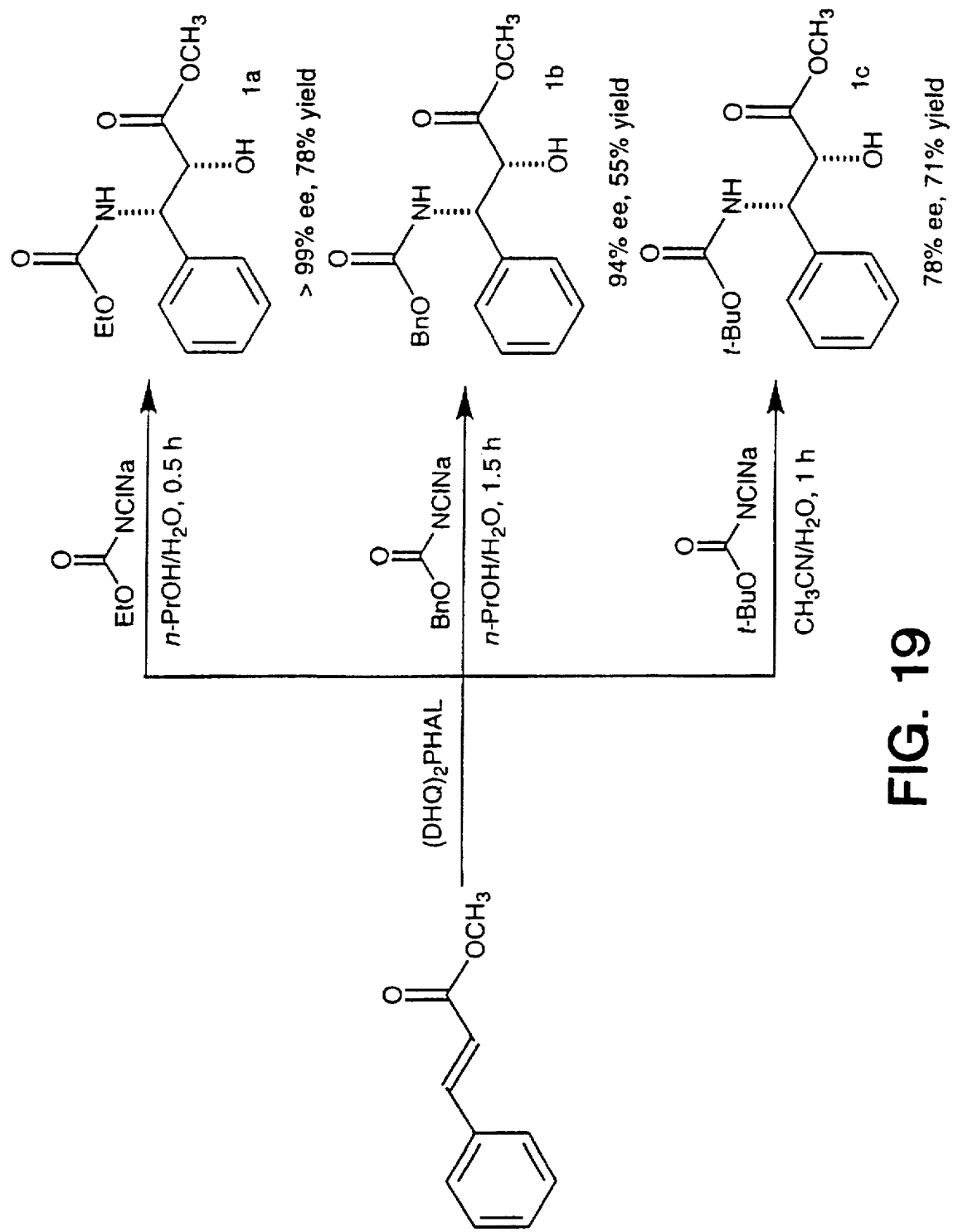
FIG. 19 illustrates the asymmetric aminohydroxylation of methylcinnamate to the corresponding hydroxy-carbamate products, from either the ethyl, benzyl or tert-butyl, N-chloro-carbamates with ee and yields indicated.
Figure 20:
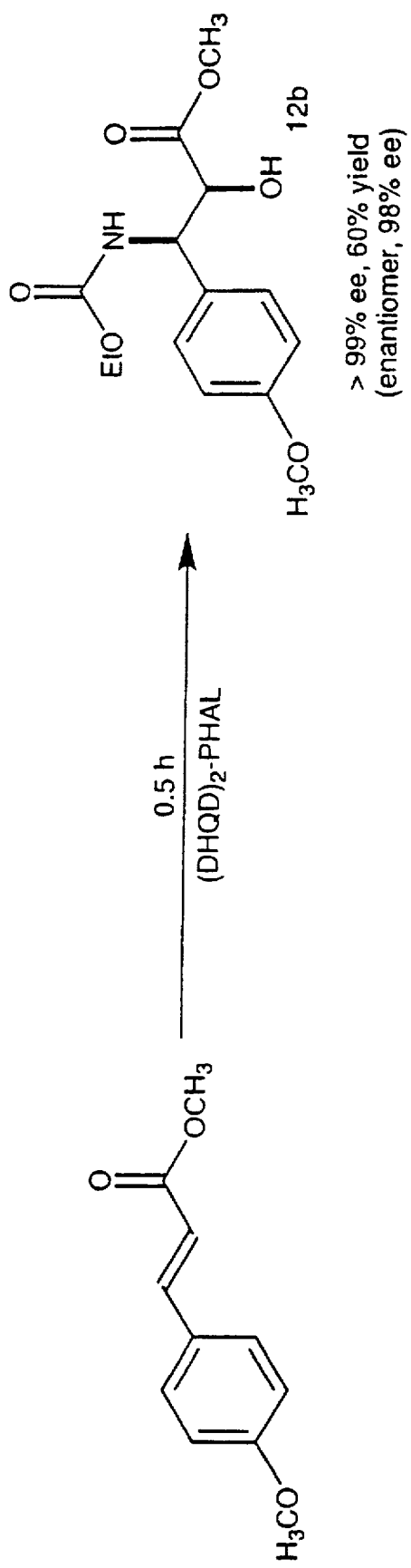
FIG. 20 illustrates the asymmetric aminohydroxylation of para-substituted methylcinnamate derivatives to the corresponding hydroxy-carbamate products with ee and yields indicated.
Figure 20:
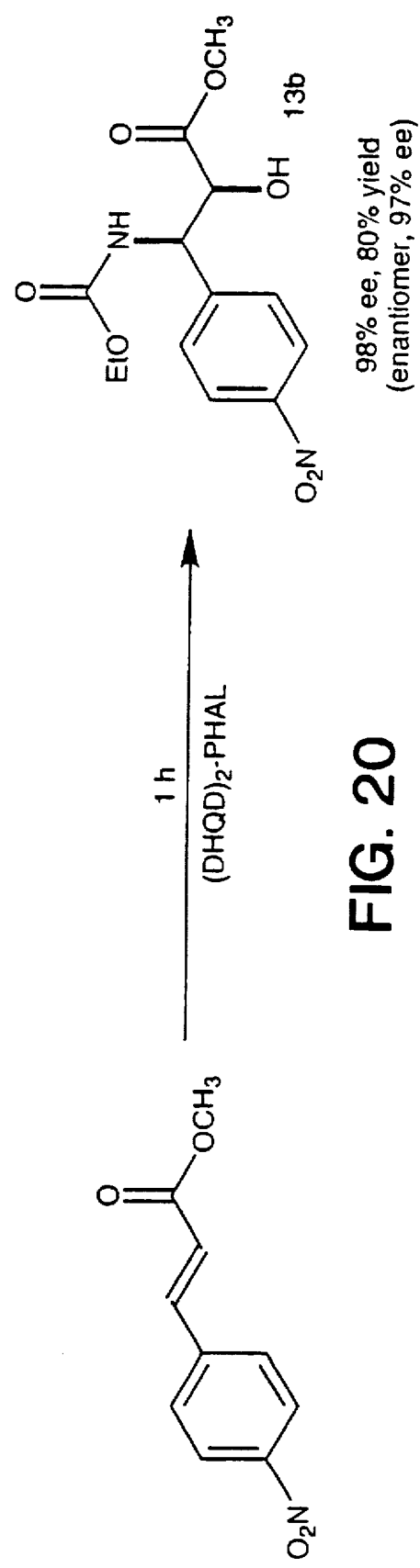
Figure 21:
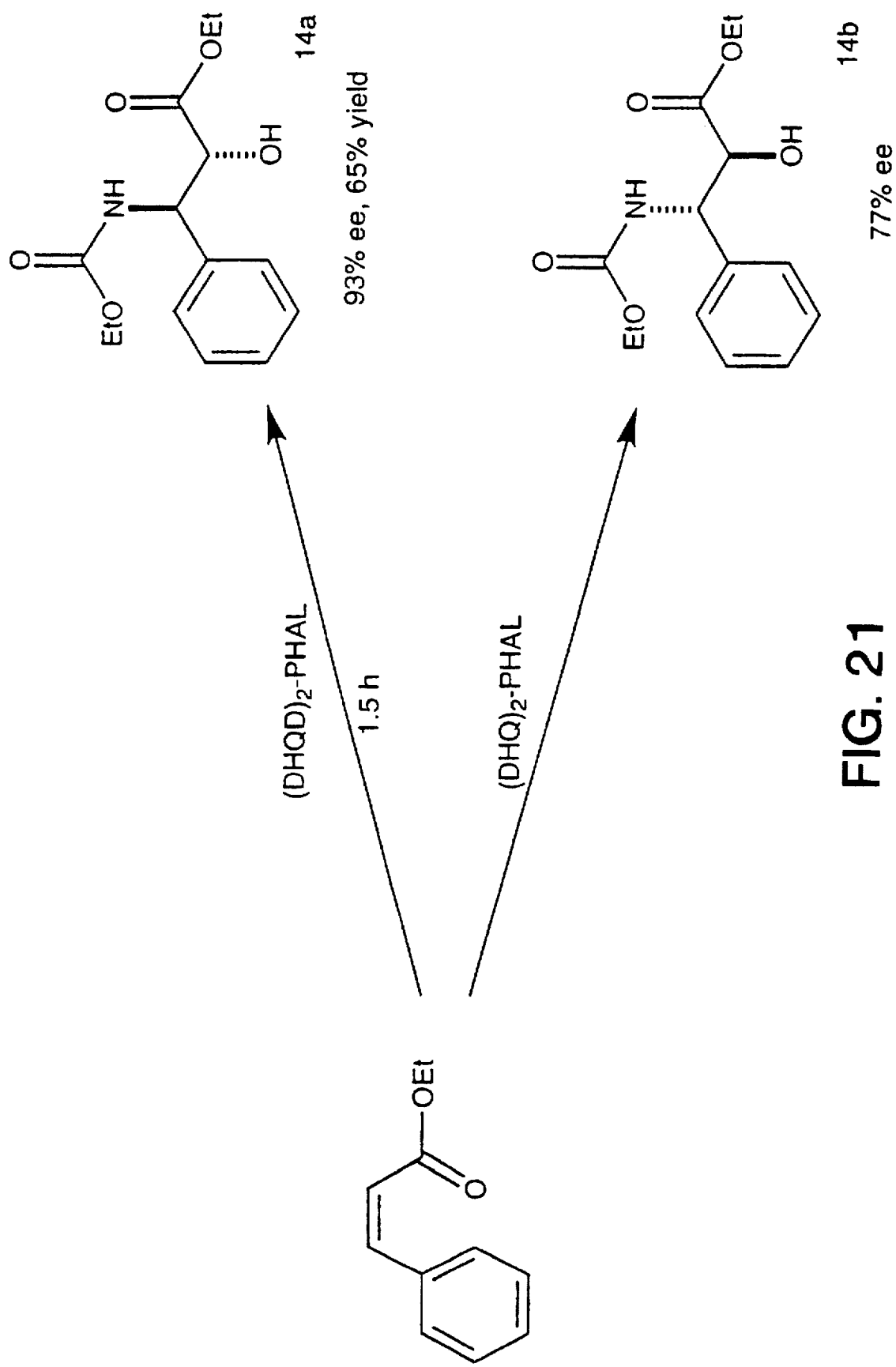
FIG. 21 illustrates the asymmetric aminohydroxylation of an aromatic cis-olefin ester to the corresponding hydroxy-carbamate products with ee and yields indicated depending on ligand used.
Figure 22:
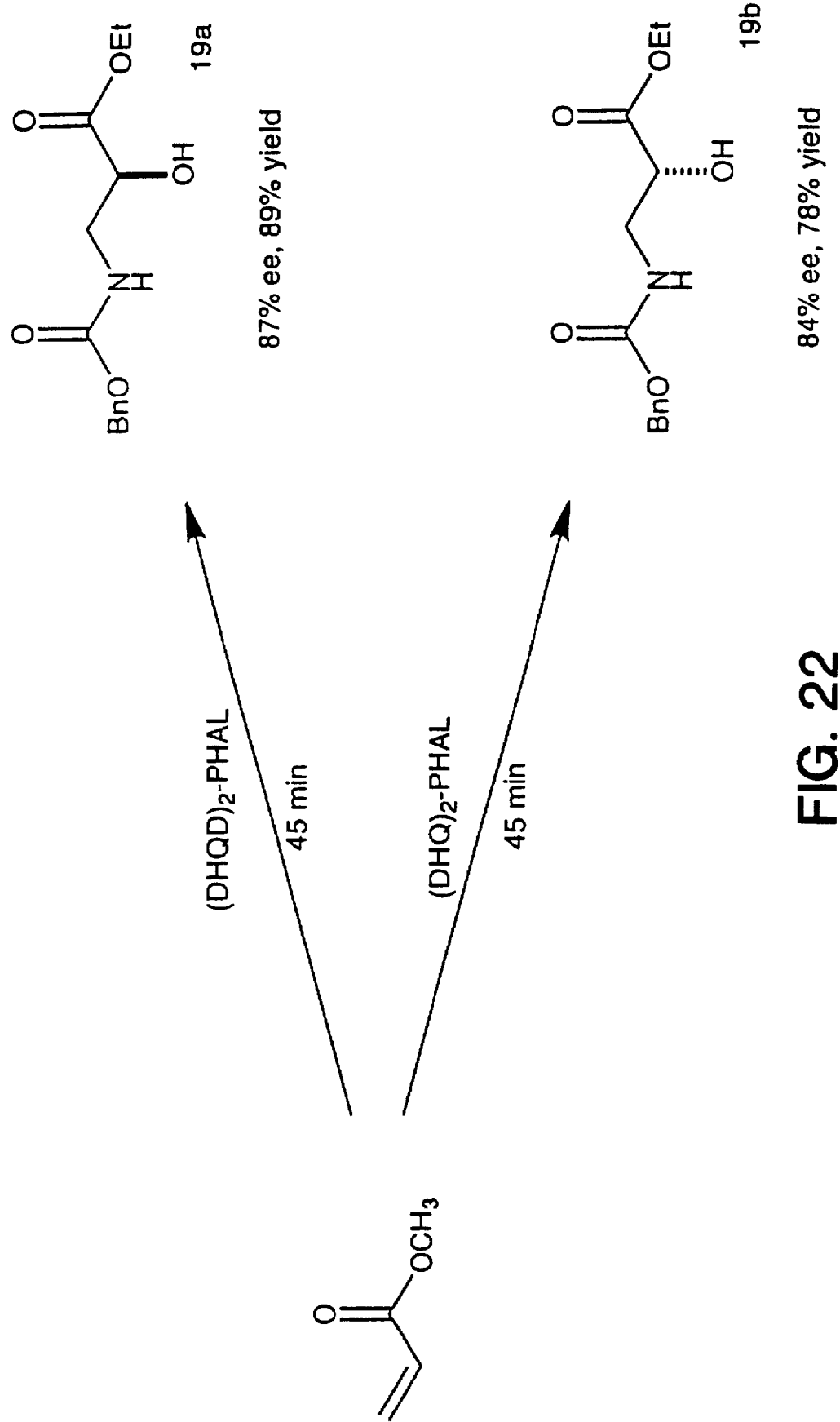
FIG. 22 illustrates the asymmetric aminohydroxylation of a vinyl ester to the corresponding hydroxy-carbamate product with ee and yields indicated depending on ligand used.
Figure 25:
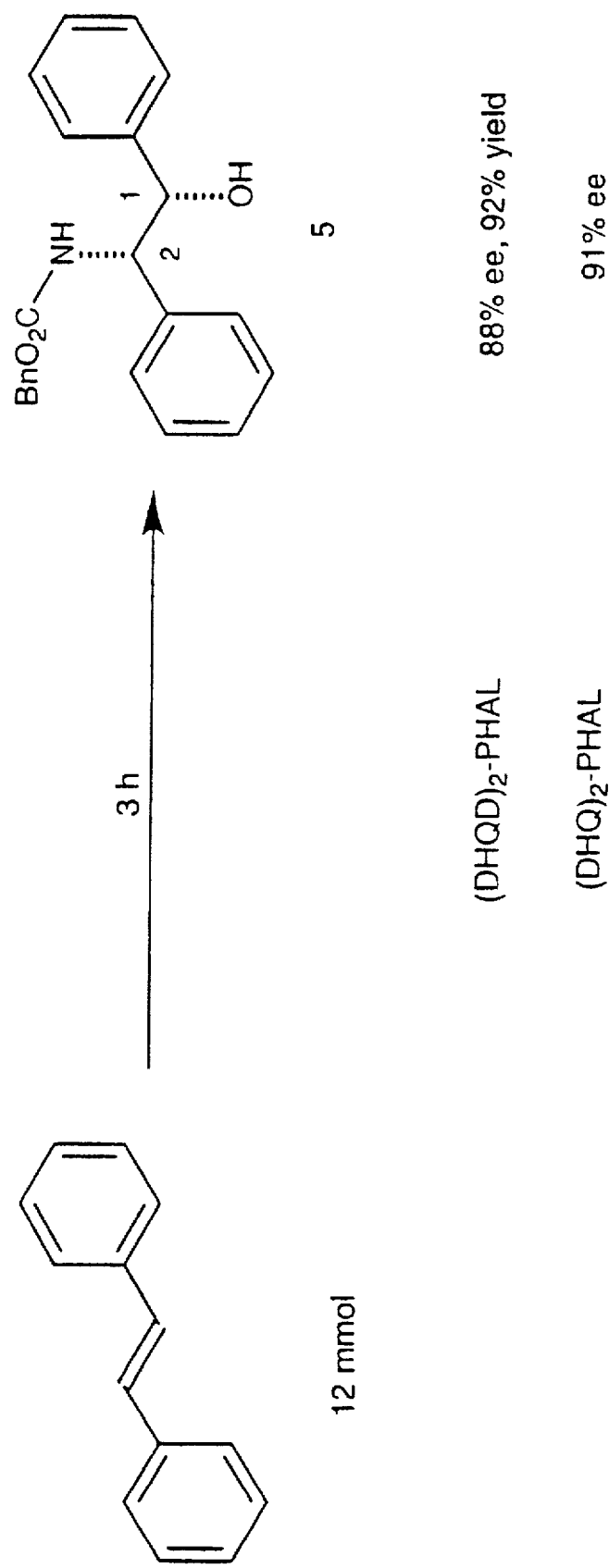
FIG. 25 illustrates the asymmetric aminohydroxylation of trans stilbene to the corresponding hydroxy-carbamate product with ee and yields indicated depending on ligand used. Product is a solid and can be recovered by filtration and purified by recrystallization.
Figure 27:
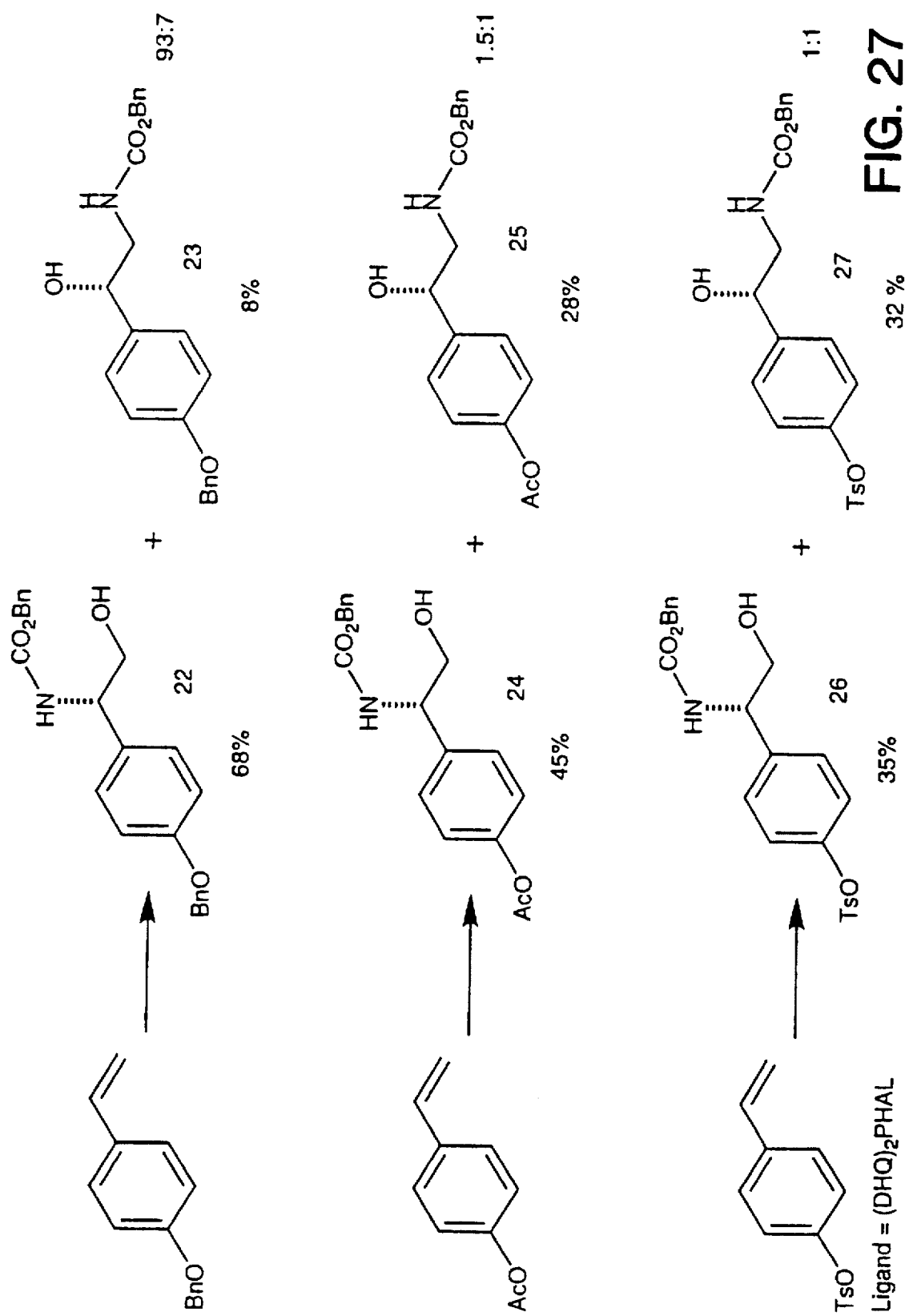
FIG. 27 illustrates the asymmetric aminohydroxylation of styrene derivatives to their corresponding hydroxy-carbamate product with ee and yields indicated depending on ligand used.
Figure 28A:
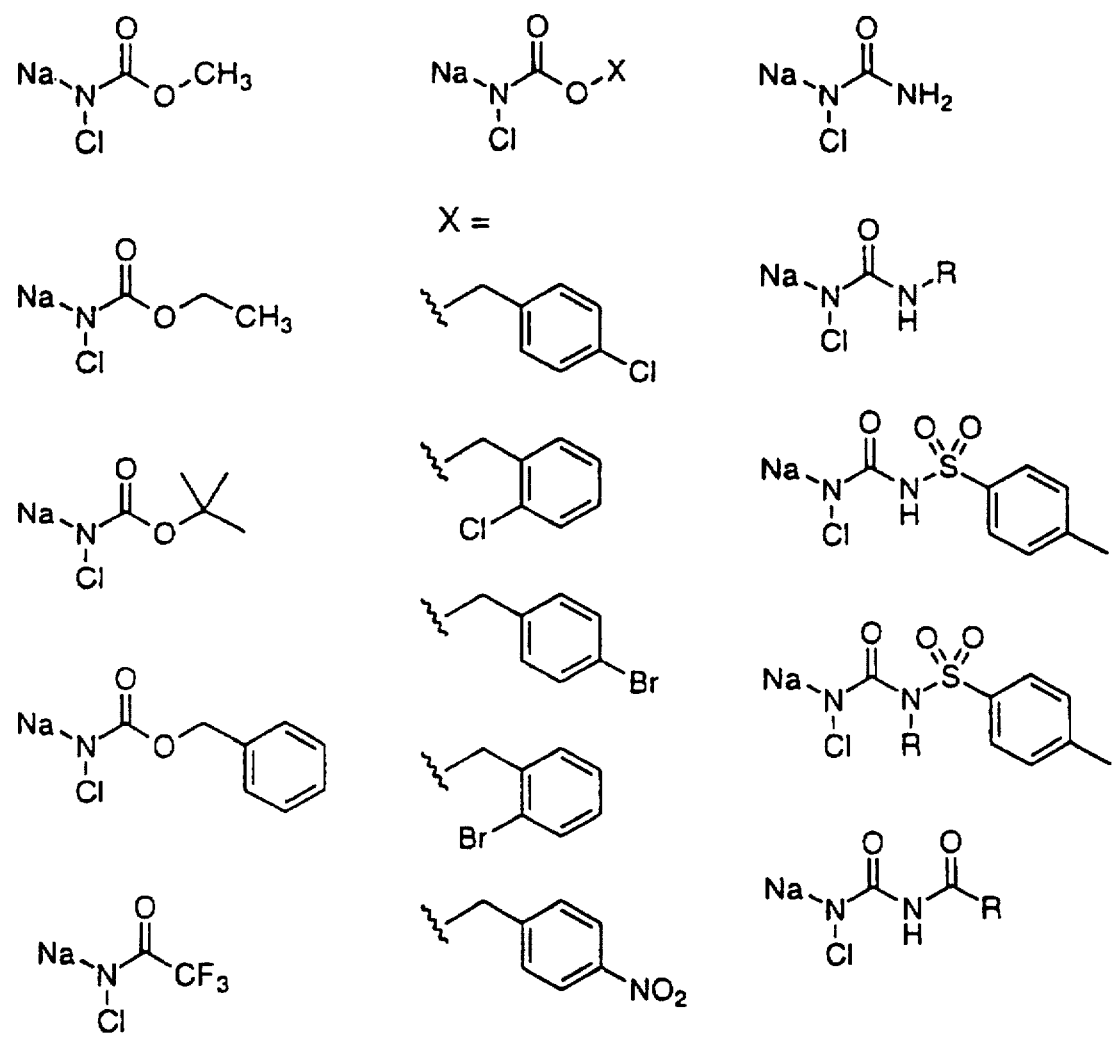
FIG. 28 illustrates a variety of sodio-N-chloro-carbamate oxidants for the asymmetric aa reaction.
Figure 28B:
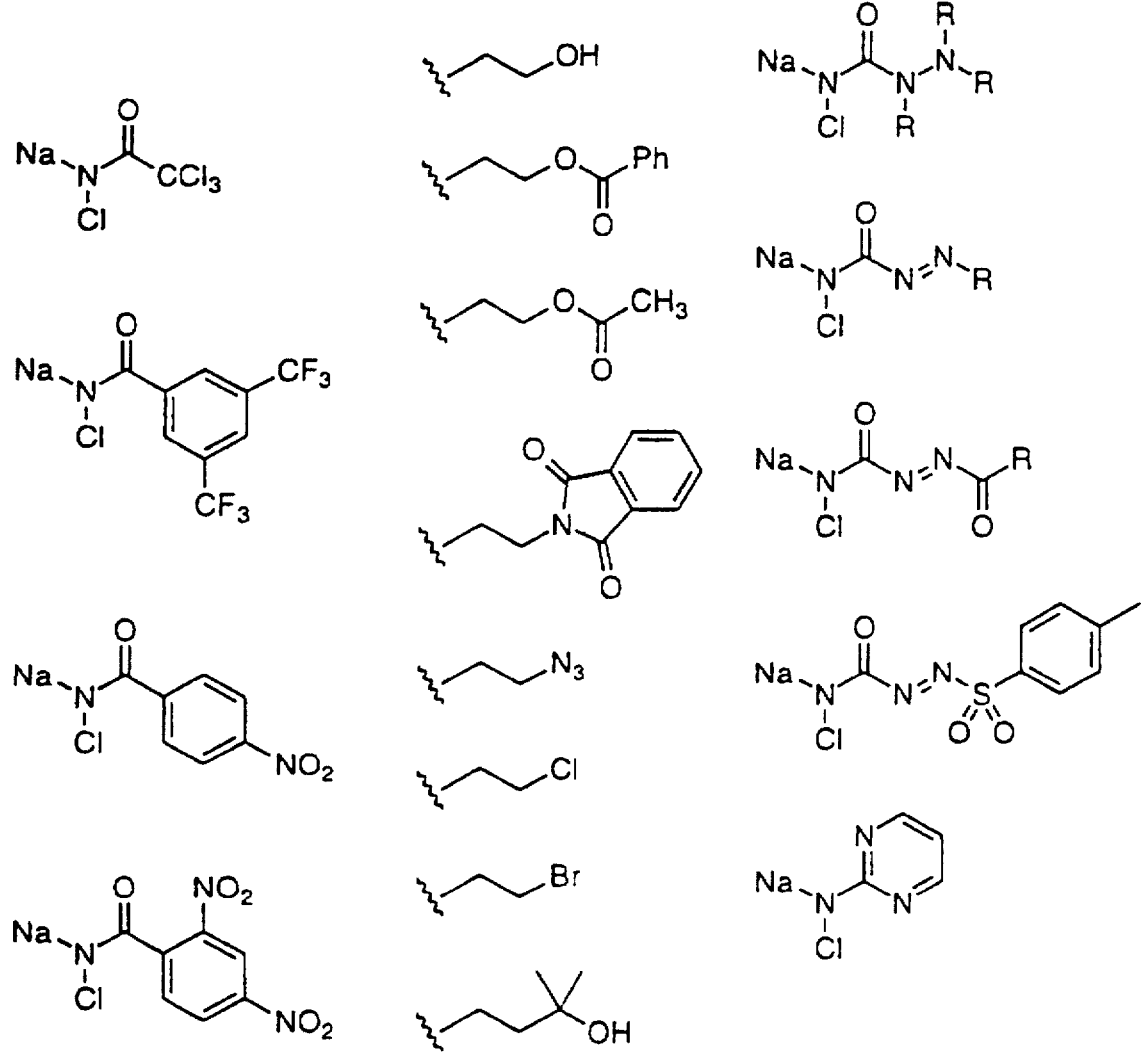

Two key points are that the ee and especially the yields are lower in the low water range (see FIGS. 11 and 12). No reaction is seen with only 2 to 4 equiv of water present which must be much less than 0.1% water These same "minuscule" amounts of water" conditions work great for the silver and mercury salts of the N-chlorocarbamates in the old catalytic aminohydroylation process with no chiral ligands present.

Solvent Concentration Variations.

In its present form the process starts to give lower selectivities for some substrates when the concentration of olefin (which of course prescribes the standard concentration of all the other species) gets much above 0.1 molar.

Ligand Variations:

The ligand can range from ca. 1 to 10 mol % (less is appropriate for lower temperatures; eg. 1% might be enough at 0° C. and 10% would probably be needed to keep the % ee at reasonable levels if the temperature reaches 35° or 40° C. In practice, the molarity of the ligand matters and the amount of ligand needed to realize the "ceiling ee" scales directly with the reaction concentration (ie if twice the volume of solvent is used, then the mol % of ligand added must also double to keep its molarity constant and correspondingly if the reaction is run twice as concentrated as usual (see general recipe below) then half of the usual mol % ligand gives the needed ligand molarity). Because the crucial binding of the ligand is an extremely rapid bimolecular process, the equilibrium constant is highly sensitive to temperature which is why the molarity of ligand needed, increases rapidly with temperature.

Osmium Variations:

The amount of Os catalyst can range from 0.5% (probably even less in the very best cases, and in any case the number will drop as the process if further improved) to 10 or even 20%. The general procedure conditions uses 4% to have fast reaction times, but 2% is good for most cases. The high loadings of 20%, for example, is needed to achieve reasonable rates with very poor substrates (this conclusion follows from the extensive experience by us and others with the AD, where in desperate situations 20 or more % Os catalyst is needed.

Temperature Variations:

For most cases, the carbamate AA process is run between 10 and 25 degrees C. There may be cases where 0 degrees-up to 35 to 40 degrees may be advantageous depending on substrate.

Deprotection conditions of carbamate to free amine t-BOC: TFA procedure: Lundt et al *Int. J. Pept. Protein Res.*, 1978, 12, 258; HCl procedure: Stahl et al. *J. Org. Chem.*, 1978, 43, 2285.

Benzyl carbamate: Hydrogenation procedure: Bergman et al *Ber.*, 1932, 65, 1192.

Ethyl and methyl carbamate: Trimethylsilyliodide procedure: Lott et al. *J. Chem. Soc. Chem. Comm* 1979, 495; HBr procedure: Wani et al *J. Am. Chem. Soc.*, 1972 94, 3631.

Transformation of R—COOH to R—COOMe

Procedure as adapted from Chan et al. *Synthesis* 1983, 201.

SYNTHESES OF A REPRESENTATIVE SET OF HYDROXYCARBAMATES

Synthesis of Compound 1

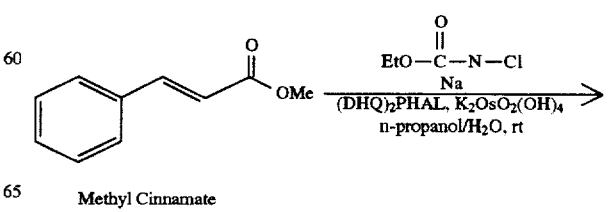

Methyl Cinnamate

15
-continued

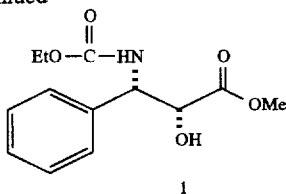

1

To a solution of NaOH (0.112 g, 3.05 mmol) in 7.5 mL of water was added ethyl carbamate (0.276 g, 3.10 mmol). The resulting solution was stirred at room temperature for 10 min and then t-butyl hypochlorite (0.331 g, 3.05 mmol; Aldrich Chemical) was added dropwise. The above solution was stirred for another 10 min and then 7.5 mL of n-propanol and (DHQ)₂-PHAL (40 mg, 0.05 mmol, 5 mol %) were added to form a homogeneous solution. The reaction mixture was immersed in a room temperature bath and added methyl cinnamate (0.162 g, 1 mmol) and K₂OsO₂(OH)₄ (14.7 mg, 0.04 mmol, 4 mol %) were then added. The reaction was stirred for 45 min with the color changing from light green to light yellow, followed by quenching by addition of aqueous sodium sulfite (sat. 6 mL); the phases were separated, and the aqueous phase was extracted with ethyl acetate (3×5 mL). The combined organic extracts were washed with water and brine, dried over MgSO₄ and the solvent concentrated to give the crude product, which also contained the ethyl carbamate by-product produced upon the reduction of the excess N-chlora-N-sodiocarbamate. Flash chromatography (6:4:1 hexane/CHCl₃/MeOH) of this material provided 0.21 g (78% yield, >99% ee) of (2R,3S) vicinal hydroxycarbamate product.

If benzyl carbamate was used, 4 mL of n-propanol was added with water to dissolve all of benzyl carbamate before adding t-butyl hypochlorite.

Synthesis of Compound 2

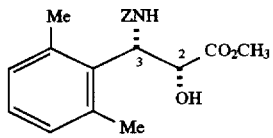

2

To a solution of NaOH (3.05 equivalents) in water (0.13 Molar; based on initial olefin concentration) was added ethyl carbamate (3.10 equivalents). The resulting solution was stirred at room temperature for 10 minutes and then t-butyl hypochlorite (3.05 equivalents; Aldrich Chemical Company) was added dropwise at 0° C. The above solution was stirred for another 10 minutes and then n-propanol (0.13 Molar; based on initial olefin concentration) and (DHQ)₂-PHAL (5 mol %) were added to form a homogeneous solution. The reaction mixture was immersed in a room temperature bath and then 2',6'-dimethyl cinnamate (1 equivalent; Aldrich) and K₂OsO₂(OH)₄ (4 mol %) were then added. The reaction was stirred for 45 minutes at room temperature with the color changing from light green to light yellow, followed by quenching by addition of aqueous sodium sulfite (saturated 0.17 Molar; based on initial olefin concentration). The phases were separated, and the aqueous phase was extracted with ethyl acetate (3×0.20M volumes). The combined organic extracts were washed with water and brine, dried over MgSO₄ and the solvent was concentrated to give the crude product, which also contained the ethyl carbamate by-product produced upon the reduction of the excess N-chlora-N-sodiocarbamate. Flash chromatography (6:4:1 hexane/CHCl₃/MeOH) of this material provided vicinal hydroxycarbamate product.

If benzyl carbamate was used, an additional 0.25M volume of n-propanol was added with water to dissolve all of benzyl carbamate before adding t-butyl hypochlorite.

Synthesis of Compound 3

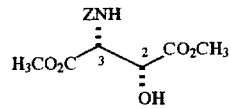

3

To a solution of NaOH (3.05 equivalents) in water (0.13 Molar; based on initial olefin concentration) was added ethyl carbamate (3.10 equivalents). The resulting solution was stirred at room temperature for 10 minutes and then t-butyl hypochlorite (3.05 equivalents; Aldrich Chemical Company) was added dropwise at 0° C. The above solution was stirred for another 10 minutes and then n-propanol (0.13 Molar; based on initial olefin concentration) and (DHQ)₂-PHAL (5 mol %) were added to form a homogeneous solution. The reaction mixture was immersed in a room temperature bath and then dimethylfumarate (1 equivalent; Aldrich) and K₂OsO₂(OH)₄ (4 mol %) were then added. The reaction was stirred for 45 minutes at room temperature with the color changing from light green to light yellow, followed by quenching by addition of aqueous sodium sulfite (saturated 0.17 Molar; based on initial olefin concentration). The phases were separated, and the aqueous phase was extracted with ethyl acetate (3×0.20M volumes). The combined organic extracts were washed with water and brine, dried over MgSO₄ and the solvent was concentrated to give the crude product, which also contained the ethyl carbamate by-product produced upon the reduction of the excess N-chlora-N-sodiocarbamate. Flash chromatography (6:4:1 hexane/CHCl₃/MeOH) of this material provided vicinal hydroxycarbamate product.

If benzyl carbamate was used, an additional 0.25M volume of n-propanol was added with water to dissolve all of benzyl carbamate before adding t-butyl hypochlorite.

Synthesis of Compound 4

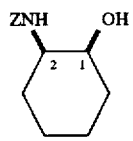

4

To a solution of NaOH (3.05 equivalents) in water (0.13 Molar; based on initial olefin concentration) was added ethyl carbamate (3.10 equivalents). The resulting solution was stirred at room temperature for 10 minutes and then t-butyl hypochlorite (3.05 equivalents; Aldrich Chemical Company) was added dropwise at 0° C. The above solution was stirred for another 10 minutes and then n-propanol (0.13 Molar; based on initial olefin concentration) and (DHQ)₂-PHAL (5 mol %) were added to form a homogeneous solution. The reaction mixture was immersed in a room temperature bath and then cyclohexene (1 equivalent; Aldrich) and K₂OsO₂(OH)₄ (4 mol %) were then added. The reaction was stirred for 45 minutes at room temperature with the color changing from light green to light yellow, followed by quenching by addition of aqueous sodium sulfite (saturated 0.17 Molar; based on initial olefin concentration).

The phases were separated, and the aqueous phase was extracted with ethyl acetate (3×0.20M volumes). The combined organic extracts were washed with water and brine, dried over MgSO$_4$ and the solvent was concentrated to give the crude product, which also contained the ethyl carbamate by-product produced upon the reduction of the excess N-chlora-N-sodiocarbamate. Flash chromatography (6:4:1 hexane/CHCl$_3$/MeOH) of this material provided vicinal hydroxycarbamate product.

If benzyl carbamate was used, an additional 0.25M volume of n-propanol was added with water to dissolve all of benzyl carbamate before adding t-butyl hypochlorite.

Synthesis of Compound 5

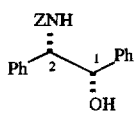

To a solution of NaOH (3.05 equivalents) in water (0.13 Molar; based on initial olefin concentration) was added ethyl carbamate (3.10 equivalents). The resulting solution was stirred at room temperature for 10 minutes and then t-butyl hypochlorite (3.05 equivalents; Aldrich Chemical Company) was added dropwise at 0° C. The above solution was stirred for another 10 minutes and then n-propanol (0.13 Molar; based on initial olefin concentration) and (DHQ)$_2$-PHAL (5 mol %) were added to form a homogeneous solution. The reaction mixture was immersed in a room temperature bath and then trans-stilbene (1 equivalent; Aldrich) and K$_2$OsO$_2$(OH)$_4$ (4 mol %) were then added. The reaction was stirred for 45 minutes at room temperature with the color changing from light green to light yellow, followed by quenching by addition of aqueous sodium sulfite (saturated 0.17 Molar; based on initial olefin concentration). The phases were separated, and the aqueous phase was extracted with ethyl acetate (3×0.20M volumes). The combined organic extracts were washed with water and brine, dried over MgSO$_4$ and the solvent was concentrated to give the crude product, which also contained the ethyl carbamate by-product produced upon the reduction of the excess N-chlora-N-sodiocarbamate. This is an example of a solution-to-solid and solid-to-solid entry—the work-up required simple filtration which provided the vicinal hydroxycarbamate product.

If benzyl carbamate was used, an additional 0.25M volume of n-propanol was added with water to dissolve all of benzyl carbamate before adding t-butyl hypochlorite.

Synthesis of Compound 6

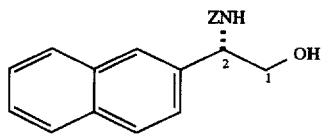

To a solution of NaOH (3.05 equivalents) in water (0.13 Molar; based on initial olefin concentration) was added ethyl carbamate (3.10 equivalents). The resulting solution was stirred at room temperature for 10 minutes and then t-butyl hypochlorite (3.05 equivalents; Aldrich Chemical Company) was added dropwise at 0° C. The above solution was stirred for another 10 minutes and then n-propanol (0.13 Molar; based on initial olefin concentration) and (DHQ)$_2$-PHAL (5 mol %) were added to form a homogeneous solution. The reaction mixture was immersed in a room temperature bath and then 2-vinylnaphthalene (1 equivalent; Aldrich) and K$_2$OsO$_2$(OH)$_4$ (4 mol %) were then added. The reaction was stirred for 45 minutes at room temperature with the color changing from light green to light yellow, followed by quenching by addition of aqueous sodium sulfite (saturated 0.17 Molar; based on initial olefin concentration). The phases were separated, and the aqueous phase was extracted with ethyl acetate (3×0.20M volumes). The combined organic extracts were washed with water and brine, dried over MgSO$_4$ and the solvent was concentrated to give the crude product, which also contained the ethyl carbamate by-product produced upon the reduction of the excess N-chlora-N-sodiocarbamate. This is an example of a solution-to-solid and solid-to-solid entry—the work-up required simple filtration which provided the vicinal hydroxycarbamate product.s If benzyl carbamate was used, an additional 0.25M volume of n-propanol was added with water to dissolve all of benzyl carbamate before adding t-butyl hypochlorite.

Synthesis of Compound 7

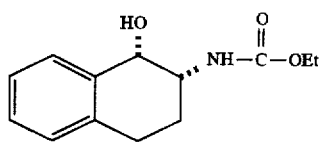

70% ee, 75% yield

To a solution of NaOH (3.05 equivalents) in water (0.13 Molar; based on initial olefin concentration) was added ethyl carbamate (3.10 equivalents). The resulting solution was stirred at room temperature for 10 minutes and then t-butyl hypochlorite (3.05 equivalents; Aldrich Chemical Company) was added dropwise at 0° C. The above solution was stirred for another 10 minutes and then n-propanol (0.13 Molar; based on initial olefin concentration) and (DHQ)$_2$-PHAL (5 mol %) were added to form a homogeneous solution. The reaction mixture was immersed in a room temperature bath and then 1,2-dihydronaphthalene (1 equivalent; Aldrich) and K$_2$OsO$_2$(OH)$_4$ (4 mol %) were then added. The reaction was stirred for 45 minutes at room temperature with the color changing from light green to light yellow, followed by quenching by addition of aqueous sodium sulfite (saturated 0.17 Molar; based on initial olefin concentration). The phases were separated, and the aqueous phase was extracted with ethyl acetate (3×0.20M volumes). The combined organic extracts were washed with water and brine, dried over MgSO$_4$ and the solvent was concentrated to give the crude product, which also contained the ethyl carbamate by-product produced upon the reduction of the excess N-chlora-N-sodiocarbamate. Flash chromatography (6:4:1 hexane/CHCl$_3$/MeOH) of this material provided vicinal hydroxycarbamate product.

If benzyl carbamate was used, an additional 0.25M volume of n-propanol was added with water to dissolve all of benzyl carbamate before adding t-butyl hypochlorite.

Synthesis of Compound 8

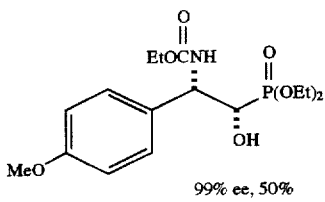

99% ee, 50%

To a solution of NaOH (3.05 equivalents) in water (0.13 Molar; based on initial olefin concentration) was added ethyl carbamate (3.10 equivalents). The resulting solution was stirred at room temperature for 10 minutes and then t-butyl hypochlorite (3.05 equivalents; Aldrich Chemical Company) was added dropwise at 0° C. The above solution was stirred for another 10 minutes and then n-propanol (0.13 Molar; based on initial olefin concentration) and $(DHQ)_2$-PHAL (5 mol %) were added to form a homogeneous solution. The reaction mixture was immersed in a room temperature bath and then trans-diethyl p-methoxy styryl phosphonate (1 equivalent; Aldrich) and $K_2OsO_2(OH)_4$ (4 mol %) were then added. The reaction was stirred for 45 minutes at room temperature with the color changing from light green to light yellow, followed by quenching by addition of aqueous sodium sulfite (saturated 0.17 Molar; based on initial olefin concentration). The phases were separated, and the aqueous phase was extracted with ethyl acetate (3×0.20M volumes). The combined organic extracts were washed with water and brine, dried over $MgSO_4$ and the solvent was concentrated to give the crude product, which also contained the ethyl carbamate by-product produced upon the reduction of the excess N-chlora-N-sodiocarbamate. Flash chromatography (6:4:1 hexane/$CHCl_3$/MeOH) of this material provided vicinal hydroxycarbamate product.

If benzyl carbamate was used, an additional 0.25M volume of n-propanol was added with water to dissolve all of benzyl carbamate before adding t-butyl hypochlorite.

Synthesis of Compound 9

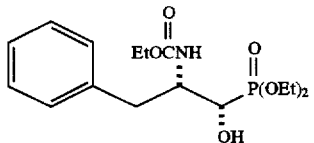

74% ee, 50%

To a solution of NaOH (3.05 equivalents) in water (0.13 Molar; based on initial olefin concentration) was added ethyl carbamate (3.10 equivalents). The resulting solution was stirred at room temperature for 10 minutes and then t-butyl hypochlorite (3.05 equivalents; Aldrich Chemical Company) was added dropwise at 0° C. The above solution was stirred for another 10 minutes and then n-propanol (0.13 Molar; based on initial olefin concentration) and $(DHQ)_2$-PHAL (5 mol %) were added to form a homogeneous solution. The reaction mixture was immersed in a room temperature bath and then trans-diethyl 3-phenyl propenyl phosphonate (1 equivalent; Aldrich) and $K_2OsO_2(OH)_4$ (4 mol %) were then added. The reaction was stirred for 45 minutes at room temperature with the color changing from light green to light yellow, followed by quenching by addition of aqueous sodium sulfite (saturated 0.17 Molar; based on initial olefin concentration). The phases were separated, and the aqueous phase was extracted with ethyl acetate (3×0.20M volumes). The combined organic extracts were washed with water and brine, dried over $MgSO_4$ and the solvent was concentrated to give the crude product, which also contained the ethyl carbamate by-product produced upon the reduction of the excess N-chlora-N-sodiocarbamate. Flash chromatography (6:4:1 hexane/$CHCl_3$/MeOH) of this material provided vicinal hydroxycarbamate product.

If benzyl carbamate was used, an additional 0.25M volume of n-propanol was added with water to dissolve all of benzyl carbamate before adding t-butyl hypochlorite.

Synthesis of Compound 10

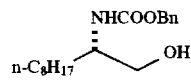

43% ee, 53% yield

To a solution of NaOH (3.05 equivalents) in water (0.13 Molar; based on initial olefin concentration) was added ethyl carbamate (3.10 equivalents). The resulting solution was stirred at room temperature for 10 minutes and then t-butyl hypochlorite (3.05 equivalents; Aldrich Chemical Company) was added dropwise at 0° C. The above solution was stirred for another 10 minutes and then n-propanol (0.13 Molar; based on initial olefin concentration) and $(DHQ)_2$-PHAL (5 mol %) were added to form a homogeneous solution. The reaction mixture was immersed in a room temperature bath and then 1-decene (1 equivalent; Aldrich) and $K_2OsO_2(OH)_4$ (4 mol %) were then added. The reaction was stirred for 45 minutes at room temperature with the color changing from light green to light yellow, followed by quenching by addition of aqueous sodium sulfite (saturated 0.17 Molar; based on initial olefin concentration). The phases were separated, and the aqueous phase was extracted with ethyl acetate (3×0.20M volumes). The combined organic extracts were washed with water and brine, dried over $MgSO_4$ and the solvent was concentrated to give the crude product, which also contained the ethyl carbamate by-product produced upon the reduction of the excess N-chlora-N-sodiocarbamate. Flash chromatography (6:4:1 hexane/$CHCl_3$/MeOH) of this material provided vicinal hydroxycarbamate product.

If benzyl carbamate was used, an additional 0.25M volume of n-propanol was added with water to dissolve all of benzyl carbamate before adding t-butyl hypochlorite.

Synthesis of Compound 11

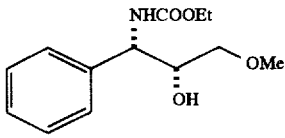

85% ee, 75% yield

To a solution of NaOH (3.05 equivalents) in water (0.13 Molar; based on initial olefin concentration) was added ethyl carbamate (3.10 equivalents). The resulting solution was stirred at room temperature for 10 minutes and then t-butyl hypochlorite (3.05 equivalents; Aldrich Chemical Company) was added dropwise at 0° C. The above solution was stirred for another 10 minutes and then n-propanol (0.13 Molar; based on initial olefin concentration) and (DHQ)$_2$-PHAL (5 mol %) were added to form a homogeneous solution. The reaction mixture was immersed in a room temperature bath and then cinnamyl alcohol methyl ether (1 equivalent; Aldrich) and K$_2$OsO$_2$(OH)$_4$ (4 mol %) were then added. The reaction was stirred for 45 minutes at room temperature with the color changing from light green to light yellow, followed by quenching by addition of aqueous sodium sulfite (saturated 0.17 Molar; based on initial olefin concentration). The phases were separated, and the aqueous phase was extracted with ethyl acetate (3×0.20M volumes). The combined organic extracts were washed with water and brine, dried over MgSO$_4$ and the solvent was concentrated to give the crude product, which also contained the ethyl carbamate by-product produced upon the reduction of the excess N-chlora-N-sodiocarbamate. Flash chromatography (6:4:1 hexane/CHCl$_3$/MeOH) of this material provided vicinal hydroxycarbamate product.

If benzyl carbamate was used, an additional 0.25M volume of n-propanol was added with water to dissolve all of benzyl carbamate before adding t-butyl hypochlorite.

Synthesis of Compound 12

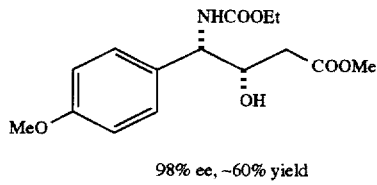

98% ee, ~60% yield

To a solution of NaOH (3.05 equivalents) in water (0.13 Molar; based on initial olefin concentration) was added ethyl carbamate (3.10 equivalents). The resulting solution was stirred at room temperature for 10 minutes and then t-butyl hypochlorite (3.05 equivalents; Aldrich Chemical Company) was added dropwise at 0° C. The above solution was stirred for another 10 minutes and then n-propanol (0.13 Molar; based on initial olefin concentration) and (DHQ)$_2$-PHAL (5 mol %) were added to form a homogeneous solution. The reaction mixture was immersed in a room temperature bath and then methyl trans 4-methoxycinnamate (1 equivalent; Aldrich) and K$_2$OsO$_2$(OH)$_4$ (4 mol %) were then added. The reaction was stirred for 45 minutes at room temperature with the color changing from light green to light yellow, followed by quenching by addition of aqueous sodium sulfite (saturated 0.17 Molar; based on initial olefin concentration). The phases were separated, and the aqueous phase was extracted with ethyl acetate (3×0.20M volumes). The combined organic extracts were washed with water and brine, dried over MgSO$_4$ and the solvent was concentrated to give the crude product, which also contained the ethyl carbamate by-product produced upon the reduction of the excess N-chlora-N-sodiocarbamate. Flash chromatography (6:4:1 hexane/CHCl$_3$/MeOH) of this material provided vicinal hydroxycarbamate product.

If benzyl carbamate was used, an additional 0.25M volume of n-propanol was added with water to dissolve all of benzyl carbamate before adding t-butyl hypochlorite.

Synthesis of Compound 13

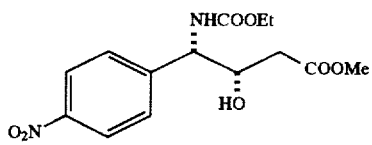

97% ee, ~80% yield

To a solution of NaOH (3.05 equivalents) in water (0.13 Molar; based on initial olefin concentration) was added ethyl carbamate (3.10 equivalents). The resulting solution was stirred at room temperature for 10 minutes and then t-butyl hypochlorite (3.05 equivalents; Aldrich Chemical Company) was added dropwise at 0° C. The above solution was stirred for another 10 minutes and then n-propanol (0.13 Molar; based on initial olefin concentration) and (DHQ)$_2$-PHAL (5 mol %) were added to form a homogeneous solution. The reaction mixture was immersed in a room temperature bath and then methyl-trans-4-nitrocinnamate (1 equivalent) and K$_2$OsO$_2$(OH)$_4$ (4 mol %) were then added. The reaction was stirred for 45 minutes at room temperature with the color changing from light green to light yellow, followed by quenching by addition of aqueous sodium sulfite (saturated 0.17 Molar; based on initial olefin concentration). The phases were separated, and the aqueous phase was extracted with ethyl acetate (3×0.20M volumes). The combined organic extracts were washed with water and brine, dried over MgSO$_4$ and the solvent was concentrated to give the crude product, which also contained the ethyl carbamate by-product produced upon the reduction of the excess N-chlora-N-sodiocarbamate. Flash chromatography (6:4:1 hexane/CHCl$_3$/MeOH) of this material provided vicinal hydroxycarbamate product.

If benzyl carbamate was used, an additional 0.25M volume of n-propanol was added with water to dissolve all of benzyl carbamate before adding t-butyl hypochlorite.

Synthesis of Compound 14

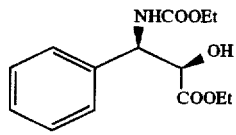

93% ee, ~50% yield

To a solution of NaOH (3.05 equivalents) in water (0.13 Molar; based on initial olefin concentration) was added ethyl carbamate (3.10 equivalents). The resulting solution was stirred at room temperature for 10 minutes and then t-butyl hypochlorite (3.05 equivalents; Aldrich Chemical Company) was added dropwise at 0° C. The above solution was stirred for another 10 minutes and then n-propanol (0.13 Molar; based on initial olefin concentration) and (DHQ)$_2$-PHAL (5 mol %) were added to form a homogeneous solution. The reaction mixture was immersed in a room temperature bath and then ethyl cis cinnamate (1 equivalent) and K$_2$OsO$_2$(OH)$_4$ (4 mol %) were then added. The reaction was stirred for 45 minutes at room temperature with the color changing from light green to light yellow, followed by quenching by addition of aqueous sodium sulfite (saturated 0.17 Molar; based on initial olefin concentration). The phases were separated, and the aqueous phase was extracted with ethyl acetate (3×0.20M volumes). The combined organic extracts were washed with water and brine, dried over MgSO$_4$ and the solvent was concentrated to give the crude product, which also contained the ethyl carbamate by-product produced upon the reduction of the excess N-chlora-N-sodiocarbamate. Flash chromatography (6:4:1 hexane/CHCl$_3$/MeOH) of this material provided vicinal hydroxycarbamate product.

If benzyl carbamate was used, an additional 0.25M volume of n-propanol was added with water to dissolve all of benzyl carbamate before adding t-butyl hypochlorite.

What is claimed is:

1. An improved method for converting an olefinic substrate to an asymmetric β-hydroxycarbamate product by asymmetric addition of an carbamoyl radical and a hydroxyl radical to the olefinic substrate, the method being of a type which employs a reaction solution which includes a carbamate as a source of the carbamoyl radical, osmium as a catalyst, a chiral ligand for enantiomerically directing said asymmetric addition, and a solvent having an organic component, the olefinic substrate and carbamate being present and soluble in stoichiometric amounts within the solvent, the osmium being present and soluble in catalytic amounts within the solvent, the chiral ligand being present and soluble within the solvent, wherein the improvement comprises:

the solvent further including an aqueous component present at 10% or greater on a volume basis.

2. An improved method for converting an olefinic substrate to an asymmetric β-hydroxycarbamate product as described in claim 1, wherein:

the aqueous component of the solvent has a range between 10% and 90% on a volume basis.

3. An improved method for converting an olefinic substrate to an asymmetric β-hydroxycarbamate product as described in claim 2, wherein:

the organic component of the solvent is selected from the group consisting of acetonitrile, tert-butanol, and n-propanol.

4. An improved method for converting an olefinic substrate to an asymmetric β-hydroxycarbamate product as described in claim 2, wherein:

the aqueous and organic components of the solvent are each approximately 50% on a volume basis.

* * * * *

UNITED STATES PATENT AND TRADEMARK OFFICE
CERTIFICATE OF CORRECTION

PATENT NO.   : 5,767,304
DATED        : June 16, 1998
INVENTOR(S)  : Sharpless et al.

It is certified that error appears in the above-identified patent and that said Letters Patent is hereby corrected as shown below:

Column 1,
Line 4, insert:
-- This invention was made with government support under Contract No. GM28384 by the National Institutes of Health and Contract No. CHE-9296055 by the National Science Foundation. The government has certain rights in the invention. --

Signed and Sealed this

Eighth Day of January, 2002

Attest:

Attesting Officer

JAMES E. ROGAN
Director of the United States Patent and Trademark Office